US008592615B2

(12) United States Patent
Kuhlman et al.

(10) Patent No.: US 8,592,615 B2
(45) Date of Patent: Nov. 26, 2013

(54) CATALYSTS, PROCESSES FOR MAKING CATALYSTS, PROCESSES FOR MAKING POLYOLEFIN COMPOSITIONS, AND POLYOLEFIN COMPOSITIONS

(75) Inventors: Roger L. Kuhlman, Lake Jackson, TX (US); Gregory T. Whiteker, Carmel, IN (US)

(73) Assignee: Dow Global Technologies, LLC, Midland, MI (US)

( * ) Notice: Subject to any disclaimer, the term of this patent is extended or adjusted under 35 U.S.C. 154(b) by 671 days.

(21) Appl. No.: 12/718,172

(22) Filed: Mar. 5, 2010

(65) Prior Publication Data

US 2010/0227990 A1 Sep. 9, 2010

Related U.S. Application Data

(60) Provisional application No. 61/158,008, filed on Mar. 6, 2009.

(51) Int. Cl.
*C07F 7/00* (2006.01)
*C07F 11/00* (2006.01)
*C07F 9/00* (2006.01)

(52) U.S. Cl.
USPC ............. 556/51; 556/57; 556/42; 526/161; 526/172; 502/113

(58) Field of Classification Search
USPC ............ 526/172, 160, 161; 556/51, 172
See application file for complete search history.

(56) References Cited

U.S. PATENT DOCUMENTS

| | | | | |
|---|---|---|---|---|
| 6,713,577 B2 * | 3/2004 | Boussie et al. | | 526/161 |
| 6,727,361 B2 * | 4/2004 | LaPointe et al. | | 546/22 |
| 6,750,345 B2 * | 6/2004 | Goh et al. | | 546/10 |
| 6,828,397 B2 * | 12/2004 | Boussie et al. | | 526/161 |
| 6,919,407 B2 * | 7/2005 | Tau et al. | | 525/191 |
| 6,998,363 B2 * | 2/2006 | Chan et al. | | 502/103 |
| 7,253,133 B2 * | 8/2007 | Sun et al. | | 502/167 |
| 7,256,296 B2 * | 8/2007 | Diamond et al. | | 548/101 |
| 7,642,216 B2 * | 1/2010 | Diamond et al. | | 502/167 |
| 7,847,099 B2 * | 12/2010 | Agapie et al. | | 546/2 |
| 7,973,116 B2 * | 7/2011 | Hagadorn et al. | | 526/172 |
| 7,989,551 B2 * | 8/2011 | Arriola et al. | | 525/268 |
| 8,158,733 B2 * | 4/2012 | Nagy et al. | | 526/172 |
| 8,258,361 B2 * | 9/2012 | Suzuki et al. | | 585/513 |
| 2007/0135575 A1 | 6/2007 | Hustad et al. | | |
| 2007/0275219 A1 | 11/2007 | Patel et al. | | |

FOREIGN PATENT DOCUMENTS

| | | | | |
|---|---|---|---|---|
| EP | 1 849 791 A1 * | 10/2007 | | C07F 11/00 |
| EP | 2174928 A1 | 4/2010 | | |
| WO | WO 2009/005003 A1 * | 1/2009 | | C07C 251/24 |

OTHER PUBLICATIONS

Domski et al., Chem. Commun., 2008, 6137-6139.*
Coates et al; Chemical Communications; 2008; p. 6137-6139; issue 46.
PCT/US10/026296 International Preliminary Report on Patentability.
PCT/US10/026296 International Search Report.
PCT/US10/026296 Written Opinion.

* cited by examiner

Primary Examiner — Rip A. Lee

(57) ABSTRACT

The present invention relates to compositions and processes of making catalysts and polyolefins. More particularly, the invention relates to snap shut catalysts, processes for making the catalysts, processes for making polyolefins using the catalysts and the polyolefins resulting therefrom.

8 Claims, 8 Drawing Sheets

¹H NMR with assignments of selected signals.

Figure 1. $^1$H NMR for N-((6-(5-(But-3-enyloxy)-2,4-dimethylphenyl)pyridin-2-yl)(phenyl)methyl)-2,6-diisopropylaniline.
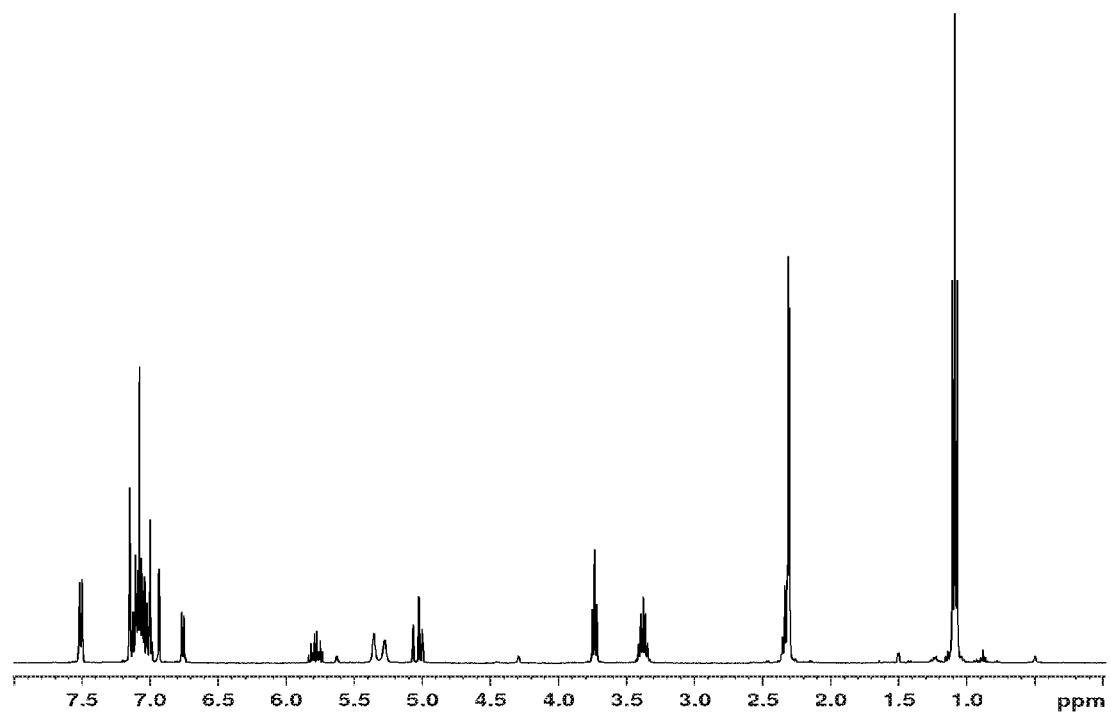

Figure 2. ¹H NMR of Reaction Mixture as "Snap-Shut" Reaction is Occurring.
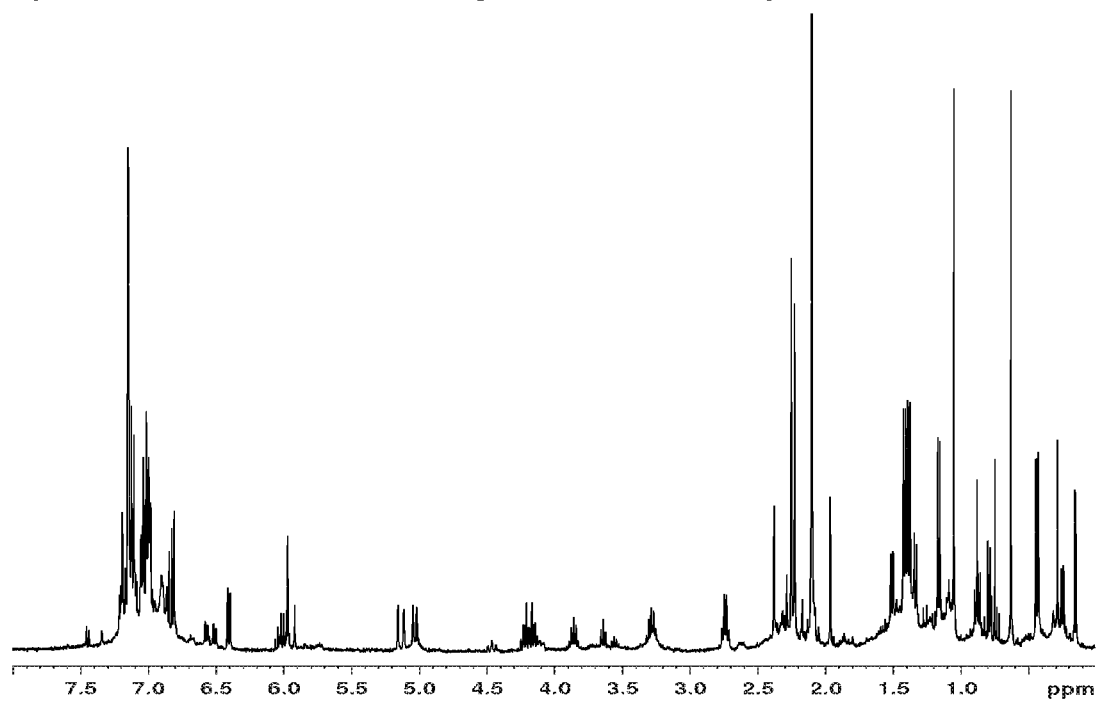

Figure 3. ¹H NMR of "Snap-Shut" Catalyst
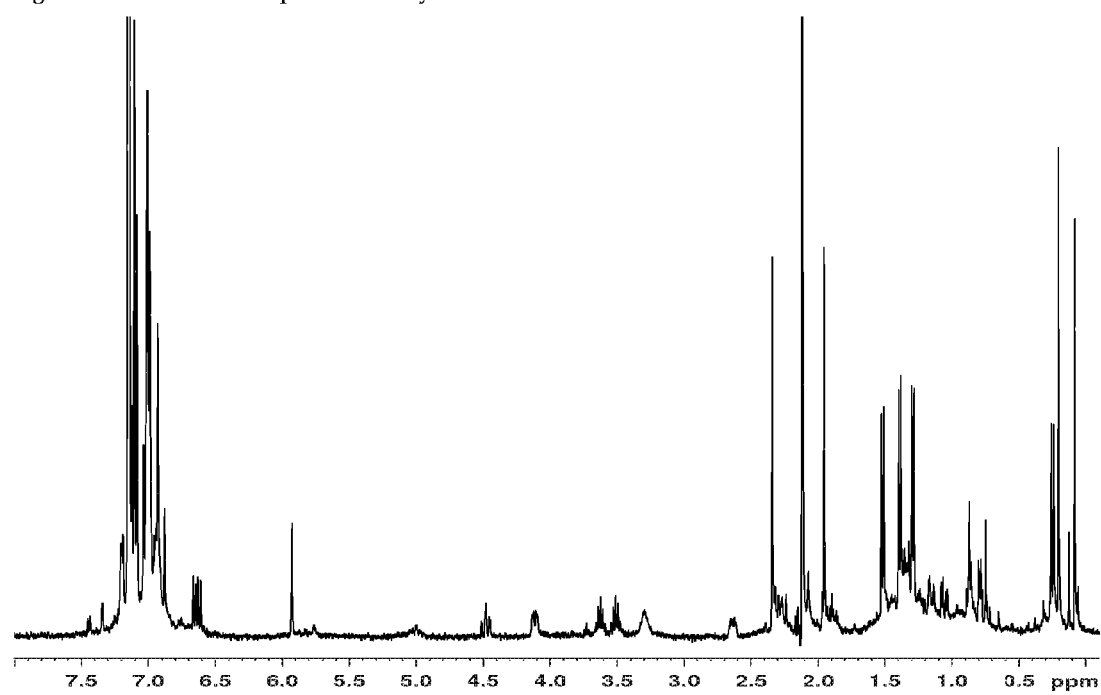

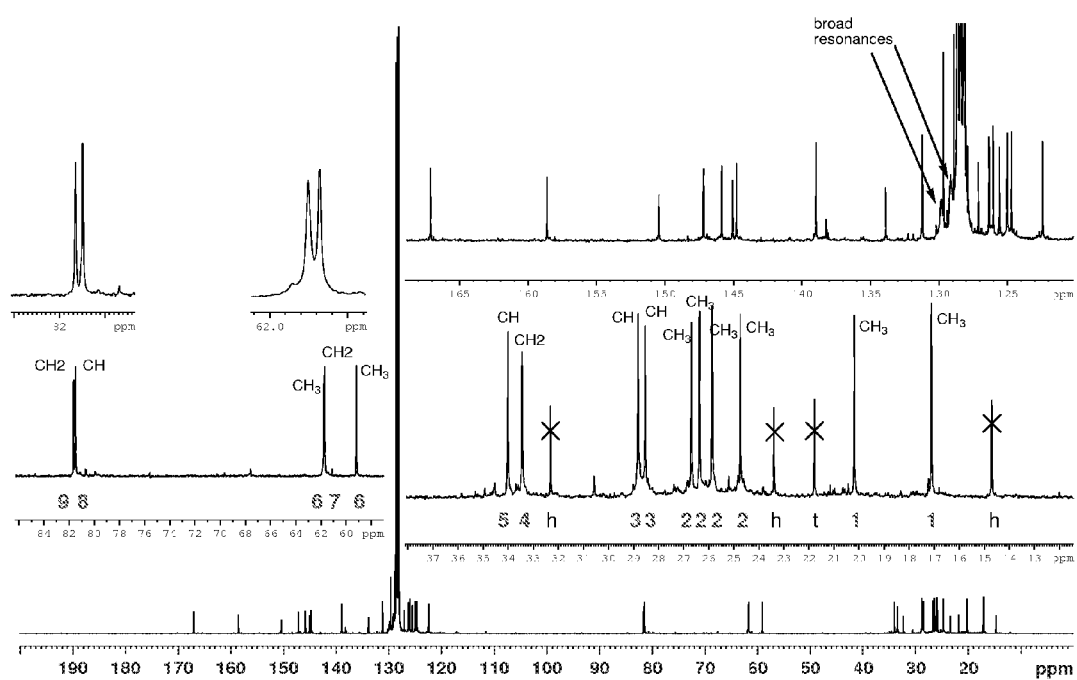
Figure 4. $^{13}C$ NMR of Snap-Shut Catalyst. Refer to Figure 5 for $^{13}C$ assignments. h = hexane; t = toluene.

Figure 5. $^1$H NMR with assignments of selected signals.
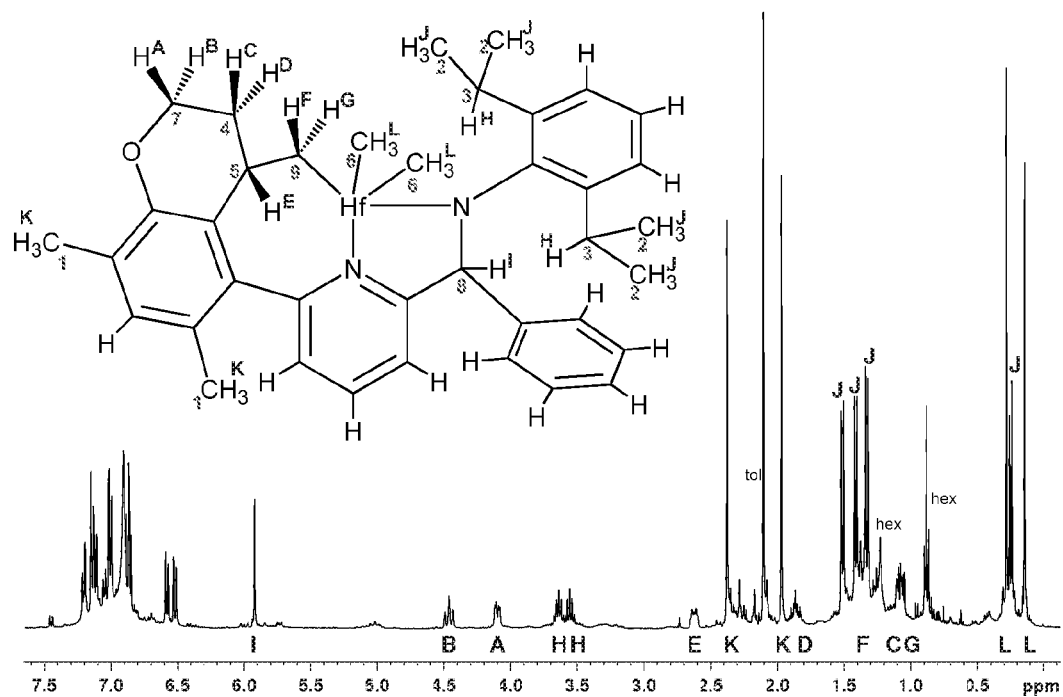

Figure 6. COSY NMR Spectrum for Snap-Shut Catalyst
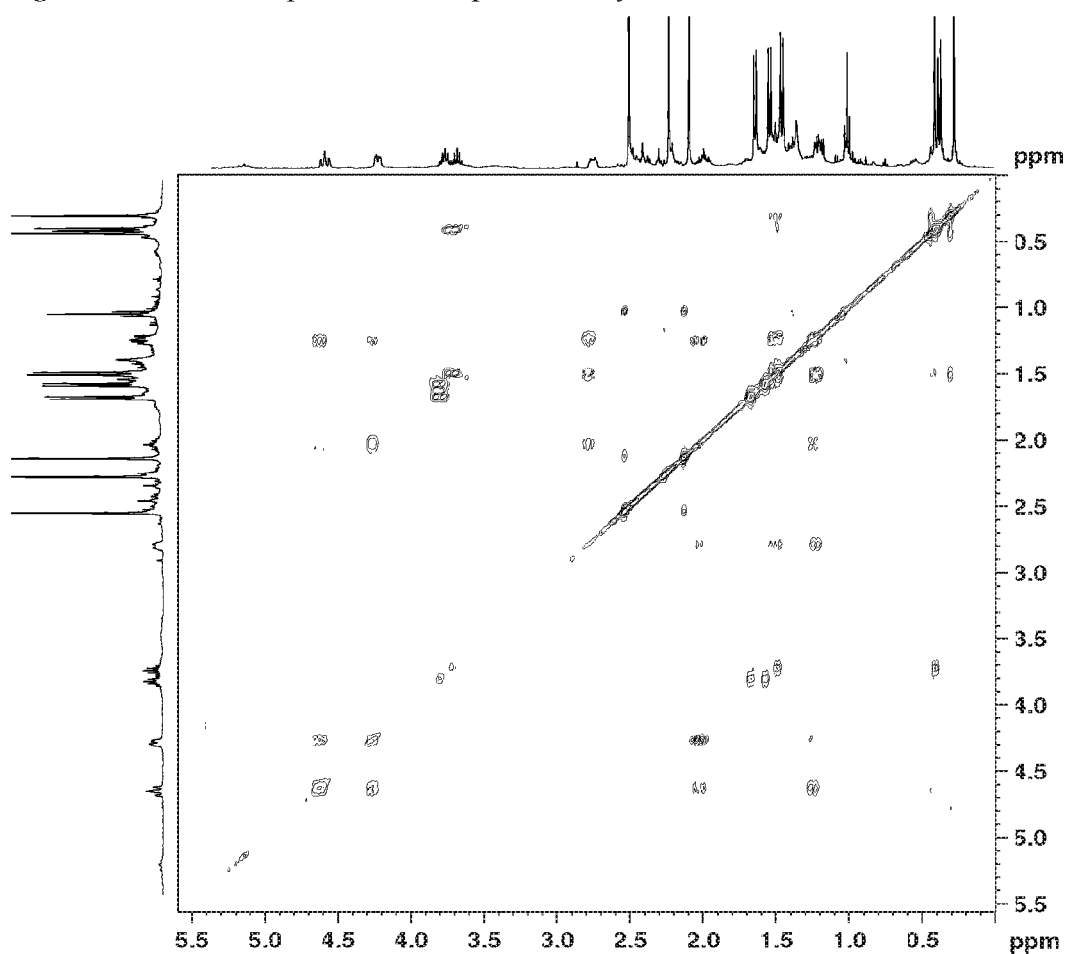

Figure 7. HSQC for Snap-Shut Catalyst.
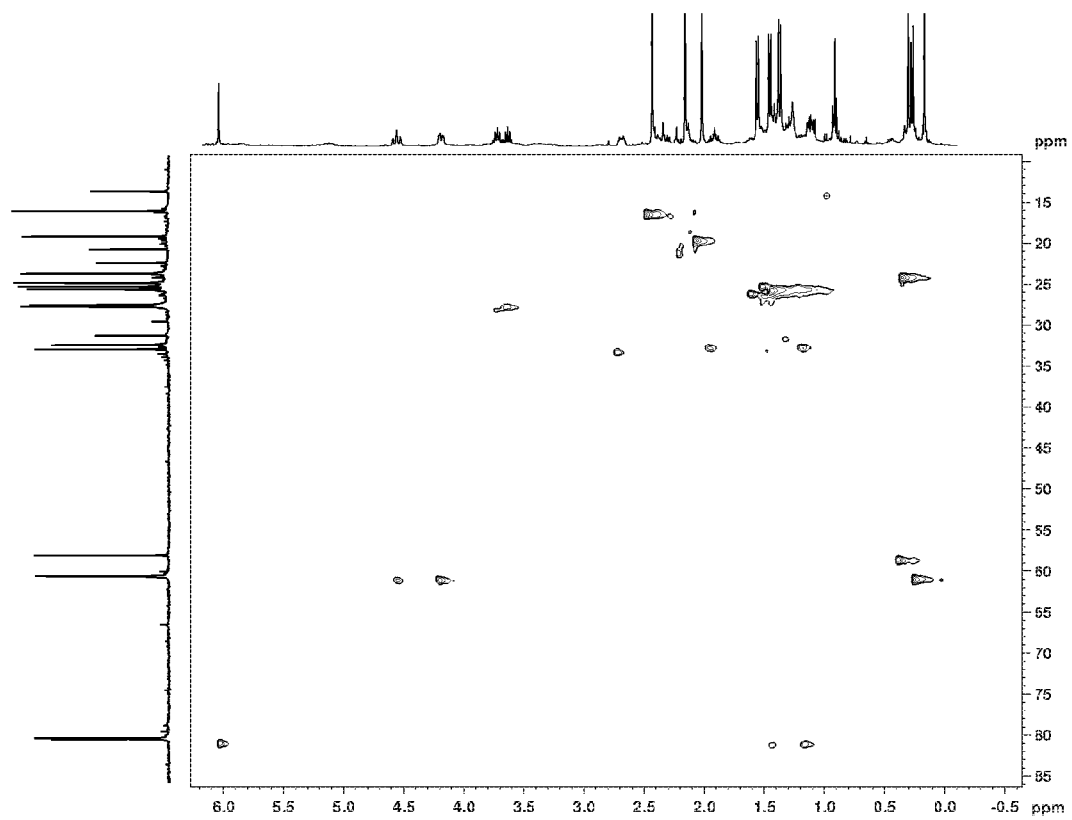

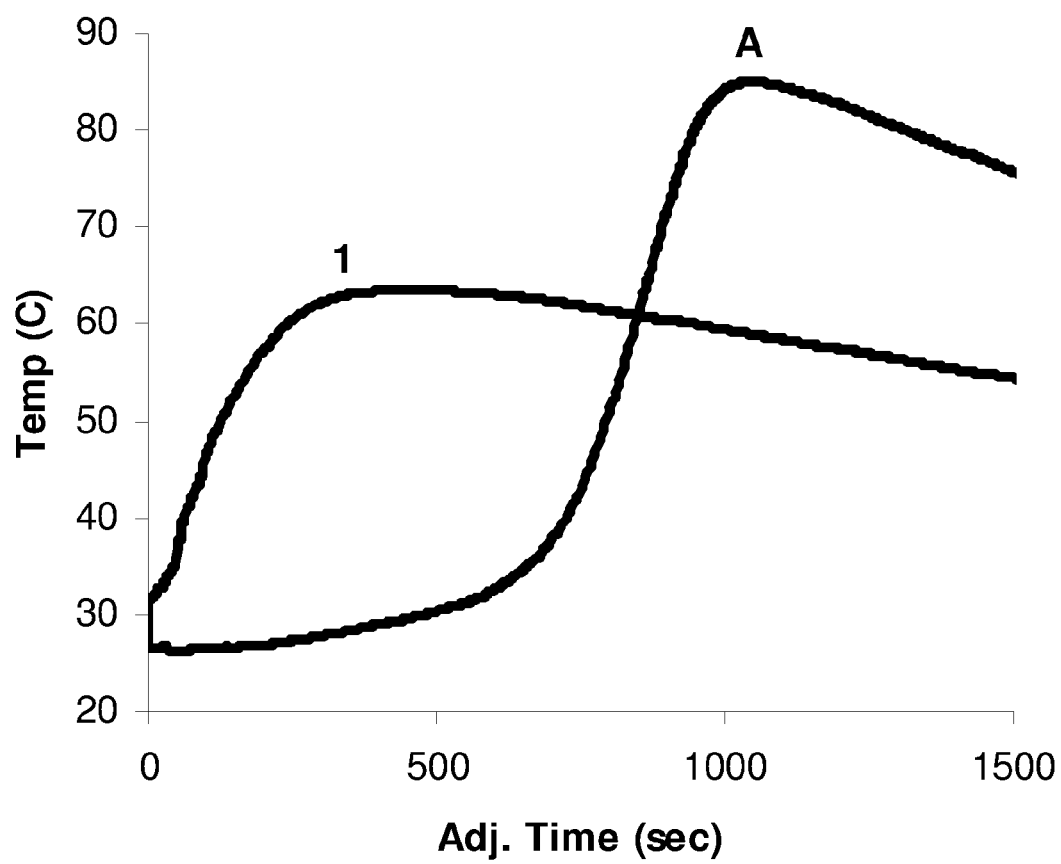
Figure 8. Comparison of A and 1 in octene polymerization. Catalysts were activated with [PhNMe$_2$H][B(C$_6$F$_5$)$_4$], and polymerizations were performed adiabatically in neat octene.

CATALYSTS, PROCESSES FOR MAKING CATALYSTS, PROCESSES FOR MAKING POLYOLEFIN COMPOSITIONS, AND POLYOLEFIN COMPOSITIONS

FIELD OF THE INVENTION

The present invention relates to catalysts, processes for making catalysts, processes for making polyolefin compositions and polyolefin compositions.

BACKGROUND OF THE INVENTION

Some catalysts, particularly those comprising a metalated aryl group, polymerize via an unusual mechanism, in which the monomer modifies the ligand framework. An example of this type of catalyst is a pyridyl-amide hafnium complex that has been described in both the open and patent literature. In such cases, the true catalyst identity is determined by the monomer(s) being polymerized. It is desirable to have a catalyst with this modification already in place to decouple the catalyst performance from the monomer makeup, better enabling catalyst optimization.

SUMMARY OF THE INVENTION

In some embodiments, the invention provides a composition corresponding to Formula (I):

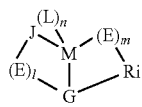

(I)

wherein:
M is a metal of any one of Groups 3 to 6 of the Periodic Table of the Elements being in a formal oxidation state of +2, +3, +4, +5, or +6; preferably, the metal is a Group 4 metal; more preferably, the metal is hafnium;
G is a Lewis base donating group containing at least one heteroatom; preferably G is a heterocyclic ring; in particular, G is a neutral (uncharged) donating group, such as a heterocycle, amine, imine, or phosphine;
E is a linking group that is preferably a divalent bridging group of from 1 to 41 atoms other than hydrogen, preferably 1 to 20 atoms other than hydrogen, and most preferably a mono- or di-$C_{1-20}$ hydrocarbyl substituted methylene or silane group; (—$CR_2$—)n wherein R is any alkyl, aryl, heteroalkyl or heteroarylalkyl; is a divalent bridging group of from 10 to 30 atoms not counting hydrogen, selected from mono- or di-aryl-substituted methylene or silylene groups or mono- or di-heteroaryl-substituted methylene or silylene groups, wherein at least one such aryl- or heteroaryl-substituent is substituted in one or both ortho-positions with a secondary or tertiary alkyl-group, a secondary or tertiary heteroalkyl group, a cycloalkyl group, or a heterocycloalkyl group;
J is a monoanionic donating group, such as alkoxy, thio, amido, phosphido, preferably amido, most preferably arylamido;
L is a leaving group, preferably a halide, N,N-di($C_{1-4}$alkyl) amido, $C_{7-10}$ aralkyl, $C_{1-20}$ alkyl, $C_{5-20}$ cycloalkyl, or tri($C_{1-4}$)alkylsilyl; a tri($C_{1-4}$)alkylsilyl-substituted $C_{1-10}$ hydrocarbyl group; or two L groups together are a $C_{4-40}$ conjugated diene;
Ri is a cyclic group selected from cycloalkyl, aryl, alkaryl, heteroaryl, heteroalkaryl, and inertly substituted derivatives thereof;
l, m, n are integers; n is selected to satisfy the valence of the metal; l and m are preferably the integers 1 to 9.

In some embodiments, the invention provides a method of making a snap shut catalyst comprising:
brominating a substituted benzene to obtain a substituted dibromo benzene;
oxidizing the substituted dibromo benzene to a substituted bromophenol via organometallic and organoboron intermediates;
alkylating the substituted bromophenol to form a bromo aryl ether which contains a pendant olefin;
reacting the bromo aryl ether with alkyl lithium and an alkyl borate to obtain an aryl boronic acid or ester which contains a pendant olefin;
reacting the aryl boronic acid or ester with a bromo pyridine-imine under Suzuki coupling conditions to obtain an arylpyridine imine which contains a pendant olefin;
alkylating the olefinic alkoxy-substituted arylpyridine imine with a Grignard or other organometallic reagent to obtain an olefinic alkoxy-substituted arylpyridine amine;
reacting the olefinic alkoxy-substituted arylpyridine amine with an alkyl lithium, metal halide and a Grignard reagent to obtain a snap shut catalyst.

In some embodiments, the invention provides a method of making a snap shut catalyst comprising:
brominating a substituted benzene to obtain a substituted dibromo benzene;
tethering an olefin to the substituted bromobenzene through a linking group E to obtain a substituted bromobenzene with a pendent olefin;
metalating the substituted bromobenzene with a pendent olefin with alkyl lithium to produce an aryllithium intermediate;
reacting the aryllithium intermediate with an alkyl borate to obtain an aryl boronic acid or ester which contains a pendant olefin;
reacting the aryl boronic acid or ester with a bromo pyridine-imine under Suzuki coupling conditions to obtain an arylpyridine imine which contains a pendant olefin;
alkylating the olefinic-substituted arylpyridine imine with a Grignard or other organometallic reagent to obtain an olefinic-substituted arylpyridine amine;
reacting the olefinic-substituted arylpyridine amine with an alkyl lithium, metal halide and a Grignard reagent to obtain a snap shut catalyst.

In some embodiments, the invention also provides a process for making polyolefins comprising:
contacting a snap shut catalyst under olefin polymerization conditions with polymerizable olefins.

In some embodiments, the invention provides a polyolefin made by contacting a snap shut catalyst under olefin polymerization conditions with polymerizable olefins.

BRIEF DESCRIPTION OF THE DRAWINGS

FIG. 1 shows $^1$H NMR for N-((6-(5-(but-3-enyloxy)-2,4-dimethylphenyl)pyridin-2-yl)(phenyl)methyl)-2,6-diisopropylaniline.
FIG. 2 shows $^1$H NMR of Reaction Mixture as Snap-Shut Reaction is Occurring
FIG. 3 shows $^1$H NMR of Snap-Shut Catalyst.
FIG. 4 shows $^{13}$C NMR of Snap-Shut Catalyst. Refer to FIG. 5 for $^{13}$C assignments. h=hexane; t=toluene.

FIG. 5 shows $^1$H NMR with assignments of selected signals.

FIG. 6 shows COSY NMR Spectrum for Snap-Shut Catalyst

FIG. 7 shows HSQC for Snap-Shut Catalyst.

FIG. 8 shows temperature profiles for adiabatic octene polymerization for a snap-shut catalyst and a comparative example.

DETAILED DESCRIPTION OF THE INVENTION

General Definitions

If and when employed herein the following terms shall have the given meaning for the purposes of this invention:

Unless otherwise noted, the phrase "Periodic Table of the Elements" refers to the official periodic table, version dated Jun. 22, 2007, published by the International Union of Pure and Applied Chemistry (IUPAC).

As used herein, the phrase "characterized by the formula" is not intended to be limiting and is used in the same way that "comprising" is commonly used. The term "independently selected" is used herein to indicate that the R groups, e.g., R1, R2, R3, R4, and R5 can be identical or different (e.g. R1, R2, R3, R4, and R5 may all be substituted alkyls or R1 and R2 may be a substituted alkyl and R3 may be an aryl, etc.). Use of the singular includes use of the plural and vice versa (e.g., a hexane solvent, includes hexanes). A named R group will generally have the structure that is recognized in the art as corresponding to R groups having that name. The terms "compound" and "complex" are generally used interchangeably in this specification, but those of skill in the art may recognize certain compounds as complexes and vice versa. For the purposes of illustration, representative certain groups are defined herein. These definitions are intended to supplement and illustrate, not preclude, the definitions known to those of skill in the art.

"Hydrocarbyl" refers to univalent hydrocarbyl radicals containing 1 to about 30 carbon atoms, preferably 1 to about 24 carbon atoms, most preferably 1 to about 12 carbon atoms, including branched or unbranched, saturated or unsaturated species, such as alkyl groups, alkenyl groups, aryl groups, and the like.

"Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom.

The term "alkyl" is used herein to refer to a branched or unbranched, saturated or unsaturated acyclic hydrocarbon radical. Suitable alkyl radicals include, for example, methyl, ethyl, n-propyl, i-propyl, 2-propenyl (or allyl), vinyl, n-butyl, t-butyl, i-butyl (or 2-methylpropyl), etc. In particular embodiments, alkyls have between 1 and 200 carbon atoms, between 1 and 50 carbon atoms or between 1 and 20 carbon atoms.

"Substituted alkyl" refers to an alkyl as just described in which one or more hydrogen atom bound to any carbon of the alkyl is replaced by another group such as a halogen, aryl, substituted aryl, cycloalkyl, substituted cycloalkyl, heterocycloalkyl, substituted heterocycloalkyl, halogen, alkylhalos (e.g., $CF_3$), hydroxy, amino, phosphido, alkoxy, amino, thio, nitro, and combinations thereof. Suitable substituted alkyls include, for example, benzyl, trifluoromethyl and the like.

The term "heteroalkyl" refers to an alkyl as described above in which one or more hydrogen atoms to any carbon of the alkyl is replaced by a heteroatom selected from the group consisting of N, O, P, B, S, Si, Sb, Al, Sn, As, Se and Ge. This same list of heteroatoms is useful throughout this specification. The bond between the carbon atom and the heteroatom may be saturated or unsaturated. Thus, an alkyl substituted with a heterocycloalkyl, substituted heterocycloalkyl, heteroaryl, substituted heteroaryl, alkoxy, aryloxy, boryl, phosphino, amino, silyl, thio, or seleno is within the scope of the term heteroalkyl. Suitable heteroalkyls include cyano, benzoyl, 2-pyridyl, 2-furyl and the like.

The term "cycloalkyl" is used herein to refer to a saturated or unsaturated cyclic non-aromatic hydrocarbon radical having a single ring or multiple condensed rings. Suitable cycloalkyl radicals include, for example, cyclopentyl, cyclohexyl, cyclooctenyl, bicyclooctyl, etc. In particular embodiments, cycloalkyls have between 3 and 200 carbon atoms, between 3 and 50 carbon atoms or between 3 and 20 carbon atoms.

"Substituted cycloalkyl" refers to cycloalkyl as just described including in which one or more hydrogen atom to any carbon of the cycloalkyl is replaced by another group such as a halogen, alkyl, substituted alkyl, aryl, substituted aryl, cycloalkyl, substituted cycloalkyl, heterocycloalkyl, substituted heterocycloalkyl, heteroaryl, substituted heteroaryl, alkoxy, aryloxy, boryl, phosphino, amino, silyl, thio, seleno and combinations thereof. Suitable substituted cycloalkyl radicals include, for example, 4-dimethylaminocyclohexyl, 4,5-dibromocyclohept-4-enyl, and the like.

The term "heterocycloalkyl" is used herein to refer to a cycloalkyl radical as described, but in which one or more or all carbon atoms of the saturated or unsaturated cyclic radical are replaced by a heteroatom such as nitrogen, phosphorous, oxygen, sulfur, silicon, germanium, selenium, or boron. Suitable heterocycloalkyls include, for example, piperazinyl, morpholinyl, tetrahydropyranyl, tetrahydrofuranyl, piperidinyl, pyrrolidinyl, oxazolinyl and the like.

"Substituted heterocycloalkyl" refers to heterocycloalkyl as just described including in which one or more hydrogen atom to any atom of the heterocycloalkyl is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heterocycloalkyl radicals include, for example, N-methylpiperazinyl, 3-dimethylaminomorpholinyl and the like.

The term "aryl" is used herein to refer to an aromatic substituent, which may be a single aromatic ring or multiple aromatic rings that are fused together, linked covalently, or linked to a common group such as a methylene or ethylene moiety. The aromatic ring(s) may include phenyl, naphthyl, anthracenyl, and biphenyl, among others. In particular embodiments, aryls have between 1 and 200 carbon atoms, between 1 and 50 carbon atoms or between 1 and 20 carbon atoms. In some embodiments herein, multi-ring moieties are substituents and in such an embodiment the multi-ring moiety can be attached at an appropriate atom. For example, "naphthyl" can be 1-naphthyl or 2-naphthyl; "anthracenyl" can be 1-anthracenyl, 2-anthracenyl or 9-anthracenyl; and "phenanthrenyl" can be 1-phenanthrenyl, 2-phenanthrenyl, 3-phenanthrenyl, 4-phenanthrenyl or 9-phenanthrenyl.

"Substituted aryl" refers to aryl as just described in which one or more hydrogen atom bound to any carbon is replaced by one or more functional groups such as alkyl, substituted alkyl, cycloalkyl, substituted cycloalkyl, heterocycloalkyl, substituted heterocycloalkyl, halogen, alkylhalos (e.g., CF3), hydroxy, amino, phosphido, alkoxy, amino, thio, nitro, and both saturated and unsaturated cyclic hydrocarbons which are fused to the aromatic ring(s), linked covalently or linked to a common group such as a methylene or ethylene moiety. The common linking group may also be a carbonyl as in benzophenone or oxygen as in diphenylether or nitrogen in diphenylamine.

The term "heteroaryl" as used herein refers to aromatic or unsaturated rings in which one or more carbon atoms of the aromatic ring(s) are replaced by a heteroatom(s) such as nitrogen, oxygen, boron, selenium, phosphorus, silicon or sulfur. Heteroaryl refers to structures that may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, pyrazole, pyrrole, furan, etc. or benzo-fused analogues of these rings are defined by the term "heteroaryl." "Substituted heteroaryl" refers to heteroaryl as just described including in which one or more hydrogen atoms bound to any atom of the heteroaryl moiety is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heteroaryl radicals include, for example, 4-N,N-dimethylaminopyridine.

The term "alkoxy" is used herein to refer to the —OZ1 radical, where Z1 is selected from the group consisting of alkyl, substituted alkyl, cycloalkyl, substituted cycloalkyl, heterocylcoalkyl, substituted heterocycloalkyl, silyl groups and combinations thereof as described herein. Suitable alkoxy radicals include, for example, methoxy, ethoxy, benzyloxy, t-butoxy, etc. A related term is "aryloxy" where Z1 is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like. As used herein the term "silyl" refers to the —SiZ1Z2Z3 radical, where each of Z1, Z2, and Z3 is independently selected from the group consisting of hydrogen, alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein the term "boryl" refers to the —BZ1Z2 group, where each of Z1 and Z2 is independently selected from the group consisting of hydrogen, alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein, the term "phosphine" refers to the group: PZ1Z2, where each of Z1 and Z2 is independently selected from the group consisting of hydrogen, substituted or unsubstituted alkyl, cycloalkyl, heterocycloalkyl, heterocyclic, aryl, substituted aryl, heteroaryl, silyl, alkoxy, aryloxy, amino and combinations thereof.

As used herein, the term "phosphine" refers to the group: PZ1Z2Z3, where each of Z1, Z3 and Z2 is independently selected from the group consisting of hydrogen, substituted or unsubstituted alkyl, cycloalkyl, heterocycloalkyl, heterocyclic, aryl, substituted aryl, heteroaryl, silyl, alkoxy, aryloxy, amino and combinations thereof.

The term "amino" is used herein to refer to the group —NZ1Z2, where each of Z1 and Z2 is independently selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "amine" is used herein to refer to the group: NZ1Z2Z3, where each of Z1, Z2 and Z2 is independently selected from the group consisting of hydrogen, alkyl, substituted alkyl, cycloalkyl, substituted cycloalkyl, heterocycloalkyl, substituted heterocycloalkyl, aryl (including pyridines), substituted aryl, heteroaryl, substituted heteroaryl, alkoxy, aryloxy, silyl and combinations thereof.

The term "thio" is used herein to refer to the group —SZ1, where Z1 is selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "seleno" is used herein to refer to the group —SeZ1, where Z1 is selected from the group consisting of hydrogen, alkyl, substituted alkyl, cycloalkyl, substituted cycloalkyl, heterocycloalkyl, substituted heterocycloalkyl, aryl, substituted aryl, beteroaryl, substituted heteroaryl, alkoxy, aryloxy, silyl and combinations thereof.

The term "saturated" refers to lack of double and triple bonds between atoms of a radical group such as ethyl, cyclohexyl, pyrrolidinyl, and the like.

The term "unsaturated" refers to the presence one or more double and triple bonds between atoms of a radical group such as vinyl, acetylide, oxazolinyl, cyclohexenyl, acetyl and the like.

Other abbreviations used herein include: "Pri" to refer to isopropyl; "But" to refer to tertbutyl; "Me" to refer to methyl; and "Et" to refer to ethyl.

The term "hetero" or "hetero-atom" refers to a non-carbon atom, especially Si, B, N, P or O. "Heteroaryl", "heteroalkyl", "heterocycloalkyl" and "heteroaralkyl" refer to aryl, alkyl, cycloalkyl, or aralkyl groups respectively, in which at least one carbon atom is replaced by a heteroatom.

"Inertly substituted" refers to substituents on a ligand that do not destroy operability of the invention.

"Polymer" means a polymeric compound prepared by polymerizing monomers, whether of the same or a different type. The generic term "polymer" embraces the terms "homopolymer," "copolymer," "terpolymer" as well as "interpolymer."

"Interpolymer" means a polymer prepared by the polymerization of at least two different types of monomers. The generic term "interpolymer" includes the term "copolymer" (which is usually employed to refer to a polymer prepared from two different monomers) as well as the term "terpolymer" (which is usually employed to refer to a polymer prepared from three different types of monomers). It also encompasses polymers made by polymerizing four or more types of monomers.

The term "multi-block copolymer" or "segmented copolymer" refers to a polymer comprising two or more chemically distinct regions or segments (referred to as "blocks") preferably joined in a linear manner, that is, a polymer comprising chemically differentiated units which are joined end-to-end with respect to polymerized ethylenic functionality, rather than in pendent or grafted fashion. In a preferred embodiment, the blocks differ in the amount or type of comonomer incorporated therein, the density, the amount of crystallinity, the crystallite size attributable to a polymer of such composition, the type or degree of tacticity (isotactic or syndiotactic), regio-regularity or regio-irregularity, the amount of branching, including long chain branching or hyper-branching, the homogeneity, or any other chemical or physical property. The multi-block copolymers are characterized by unique distributions of both polydispersity index (PDI or Mw/Mn), block length distribution, and/or block number distribution due to the unique process making of the copolymers. More specifically, when produced in a continuous process, the multi-block polymers often possess PDI from 1.7 to 2.9, preferably from 1.8 to 2.5, more preferably from 1.8 to 2.2, and most preferably from 1.8 to 2.1.

The term, "shuttling agent" refers to a compound or mixture of compounds employed in the composition of the present invention that is capable of causing polymeryl exchange between at least two active catalyst sites of the catalysts included in the composition under the conditions of the polymerization. That is, transfer of a polymer fragment occurs both to and from one or more of the active catalyst sites. In contrast to a shuttling agent, a "chain transfer agent" causes termination of polymer chain growth and amounts to a one-time transfer of growing polymer from the catalyst to the transfer agent.

"Suzuki coupling conditions" refers to reaction conditions that effect the formation of a bond between two like or unlike aryl or heteroaryl groups from an aryl halide or pseudohalide, and an aryl boronic acid or ester. Typically, a palladium catalyst and a base are used to effect the reaction.

The term "snap shut reaction" means an intramolecular cyclization that occurs via insertion of an olefinic or other unsaturated group into a metal-aryl bond. A "snap shut catalyst" is a metal cycloalkylmethyl complex wherein the cycloalkyl ring is fused to a substituted or unsubstituted benzene ring. The cycloalkyl ring may include heteroatoms such as oxygen, nitrogen or silicon. When the unsaturated group that inserts into a metal-aryl bond has at least one heteroatom, then at least one heteroatom is bound to the metal.

In the following description, all numbers disclosed herein are approximate values, regardless whether the word "about" or "approximate" is used in connection therewith. They may vary by 1 percent, 2 percent, 5 percent, or, sometimes, 10 to 20 percent. Whenever a numerical range with a lower limit, $R^L$ and an upper limit, $R^U$, is disclosed, any number falling within the range is specifically disclosed. In particular, the following numbers within the range are specifically disclosed: $R=R^L+k*(R^U-R^L)$ wherein k is a variable ranging from 1 percent to 100 percent with a 1 percent increment, i.e., k is 1 percent, 2 percent, 3 percent, 4 percent, percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed.

"Density" is tested in accordance with ASTM D792.

"Melt Index ($I_2$)" is determined according to ASTM D1238 using a weight of 2.16 kg at 190° C. for polymers comprising ethylene as the major component in the polymer.

"Melt Flow Rate (MFR)" is determined for according to ASTM D1238 using a weight of 2.16 kg at 230° C. for polymers comprising propylene as the major component in the polymer.

"Molecular weight distribution" or MWD is measured by conventional GPC per the procedure described by Williams, T.; Ward, I. M. *Journal of Polymer Science, Polymer Letters Edition* (1968), 6(9), 621-624. Coefficient B is 1. Coefficient A is 0.4316.

By the term "overnight" is meant approximately 16-18 hours.

The present invention comprises a composition corresponding to Formula (I):

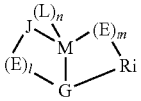

wherein:

M is a metal of any one of Groups 3 to 6 of the Periodic Table of the Elements being in a formal oxidation state of +2, +3, +4, +5, or +6; preferably, the metal is a Group 4 metal; more preferably, the metal is hafnium;

G is a Lewis base donating group containing at least one heteroatom; preferably G is a heterocyclic ring; in particular, G is a neutral (uncharged) donating group, such as a heterocycle, amine, imine, or phosphine.

E is a linking group that is preferably a divalent bridging group of from 1 to 41 atoms other than hydrogen, preferably 1 to 20 atoms other than hydrogen, and most preferably a mono- or di-$C_{1-20}$ hydrocarbyl substituted methylene or silane group; (—$CR_2$—)n wherein R is any alkyl, aryl, heteroalkyl or heteroarylalkyl; is a divalent bridging group of from 10 to 30 atoms not counting hydrogen, selected from mono- or di-aryl-substituted methylene or silylene groups or mono- or di-heteroaryl-substituted methylene or silylene groups, wherein at least one such aryl- or heteroaryl-substituent is substituted in one or both ortho-positions with a secondary or tertiary alkyl-group, a secondary or tertiary heteroalkyl group, a cycloalkyl group, or a heterocycloalkyl group; J is a monoanionic donating group, such as alkoxy (—O), alkyl sulfide (—S), amido (—NR), phosphide (—PR), preferably amido, most preferably arylamido (—NAr);

L is a leaving group, preferably a halide, N,N-di($C_{1-4}$alkyl) amido, $C_{7-10}$ aralkyl, $C_{1-20}$ alkyl, $C_{5-20}$ cycloalkyl, or tri($C_{1-4}$)alkylsilyl; a tri($C_{1-4}$)alkylsilyl-substituted $C_{1-10}$ hydrocarbyl group; or two L groups together are a $C_{4-40}$ conjugated diene;

Ri is a cyclic group selected from cycloalkyl, aryl, alkaryl, heteroaryl, heteroalkaryl, and inertly substituted derivatives thereof;

l, m, n are integers; n is selected to satisfy the valence of the metal; l and m are preferably the integers 1 to 9.

Preferred compositions of the invention, include, but are not necessarily limited to the following:

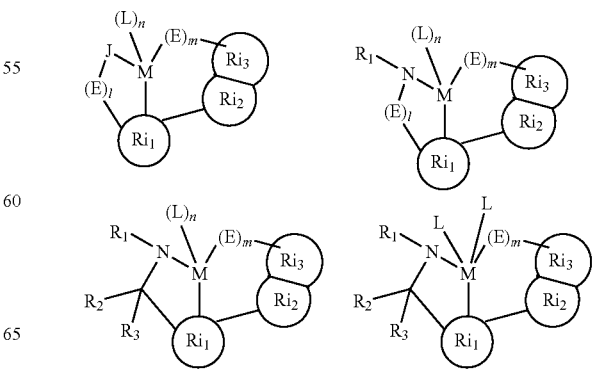

-continued

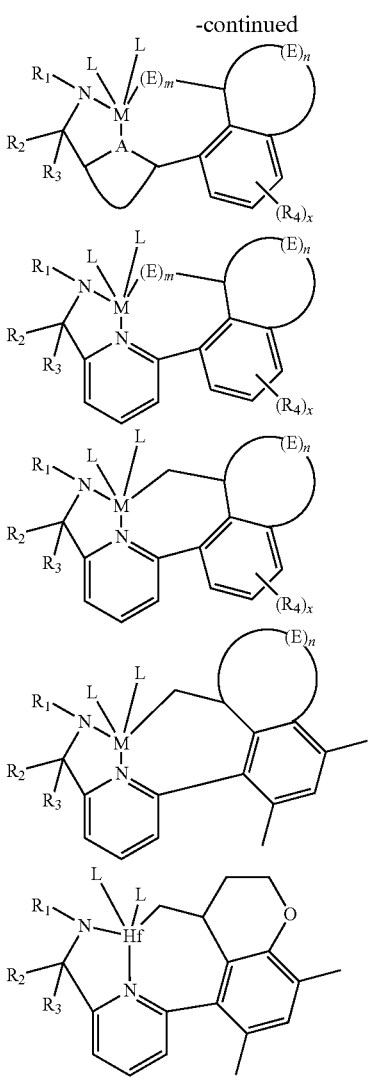

wherein L, M, E, m and n are as defined above;

$Ri_1$, $Ri_2$, and $Ri_3$ are cyclic groups selected from cycloalkyl, aryl, alkaryl, heteroaryl, heteroalkaryl, and inertly substituted derivatives thereof;

$R_1$, $R_2$, $R_3$ and $R_4$ are selected from alkyl, cycloalkyl, heteroalkyl, cycloheteroalkyl, aryl, heteroaryl and inertly substituted derivatives thereof; and, x and l are integers.

Preferred compositions are those corresponding to Formula (II):

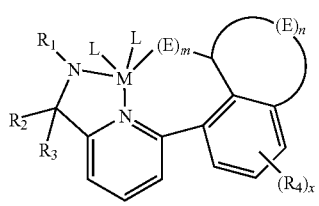

(II)

wherein L, M, E, $R_1$, $R_2$, $R_3$ and $R_4$, and x, m and n are as defined above. Preferably, x, m and n are integers from 1 to 9, preferably m is an integer from 1 to 4, most preferably, m is 1.

Preferably each catalyst molecule is essentially the same as every other catalyst molecule. By this is meant that the chemical structures of the molecules are substantially the same.

Bonds, optional bonds and electron donative interactions are represented by lines, dotted lines and arrows respectively.

Preferred specific embodiments of the invention include, but are not necessarily limited to, the following:

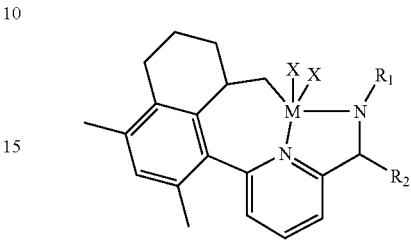

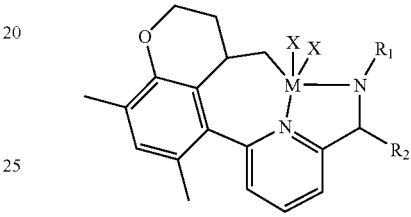

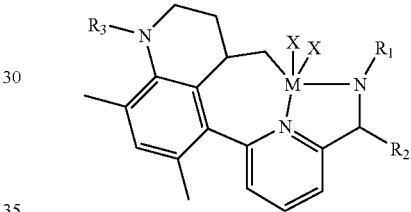

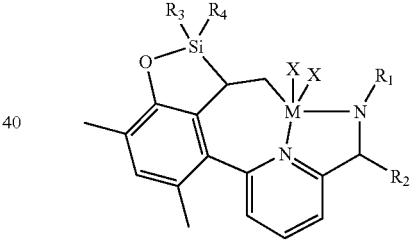

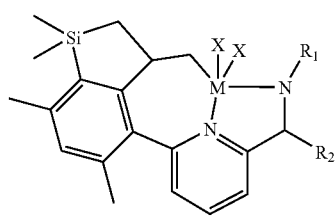

11
-continued
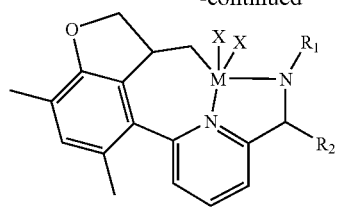
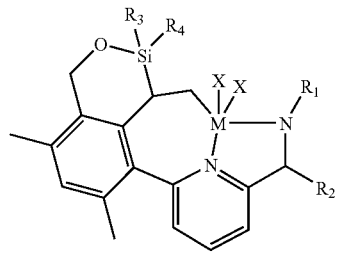
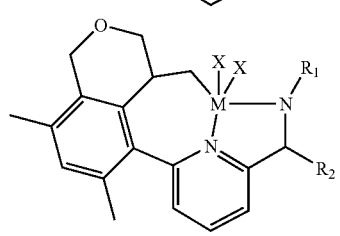
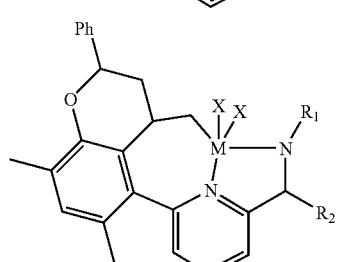
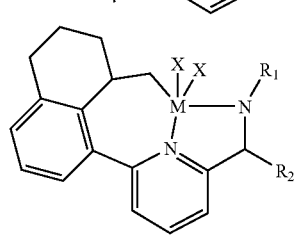
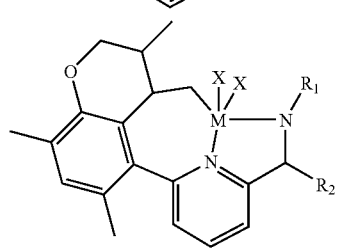
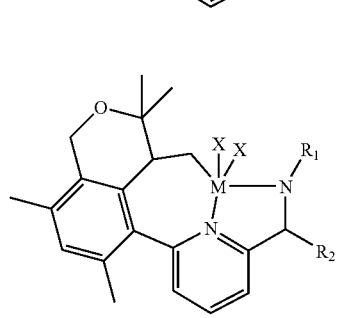
12
-continued
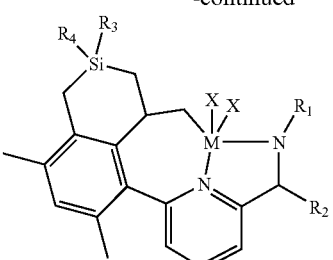
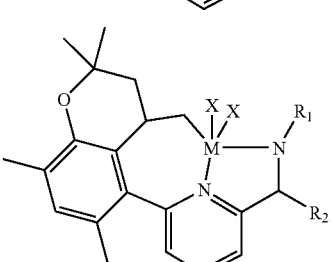
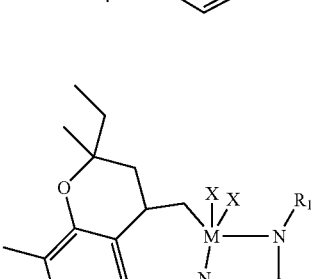
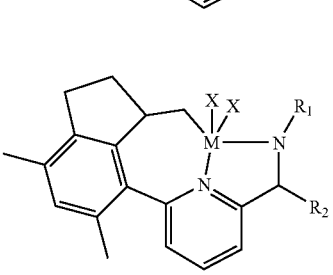
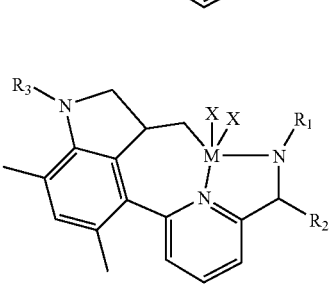
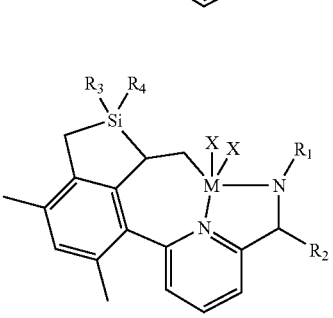

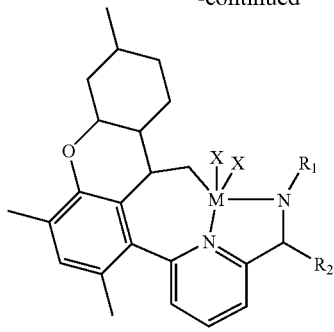

wherein M, E, $R_1$, $R_2$, $R_3$ and $R_4$, and x, m and n are as defined above; and, X is a leaving group, preferably a halide, N,N-di($C_{1-4}$alkyl)amido, $C_{7-10}$ aralkyl, or $C_{1-20}$ alkyl.

Cocatalysts

As one skilled in the art will appreciate it may be useful to combine the pre-catalyst or synthesized catalyst with a suitable cocatalyst, preferably a cation forming cocatalyst, a strong Lewis acid, or a combination thereof. In a preferred embodiment, a shuttling agent, if employed, is employed both for purposes of chain shuttling and as the cocatalyst component of the catalyst composition.

The metal complexes desirably are rendered catalytically active by combination with a cation forming cocatalyst, such as those previously known in the art for use with Group 4 metal olefin polymerization complexes. Suitable cation forming cocatalysts for use herein include neutral Lewis acids, such as $C_{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluoro-phenyl)borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, or ferrocenium-, lead- or silver salts of compatible, noncoordinating anions; and combinations of the foregoing cation forming cocatalysts and techniques. The foregoing activating cocatalysts and activating techniques have been previously taught with respect to different metal complexes for olefin polymerizations in the following references: EP-A-277,003, U.S. Pat. No. 5,153,157, U.S. Pat. No. 5,064,802, U.S. Pat. No. 5,321,106, U.S. Pat. No. 5,721,185, U.S. Pat. No. 5,350,723, U.S. Pat. No. 5,425,872, U.S. Pat. No. 5,625,087, U.S. Pat. No. 5,883,204, U.S. Pat. No. 5,919,983, U.S. Pat. No. 5,783,512, WO 99/15534, and WO99/42467.

Combinations of neutral Lewis acids, especially the combination of a trialkyl aluminum compound having from 1 to 4 carbons in each alkyl group and a halogenated tri(hydrocarbyl)boron compound having from 1 to 20 carbons in each hydrocarbyl group, especially tris(pentafluorophenyl)borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane may be used as activating cocatalysts. Preferred molar ratios of metal complex:tris(pentafluorophenyl)borane:alumoxane are from 1:1:1 to 1:5:20, more preferably from 1:1:1.5 to 1:5:10.

Suitable ion forming compounds useful as cocatalysts in one embodiment of the present invention comprise a cation which is a Bronsted acid capable of donating a proton, and a compatible, noncoordinating anion, K. As used herein, the term "noncoordinating" means an anion or substance which either does not coordinate to the Group 4 metal containing precursor complex and the catalytic derivative derived there from, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

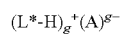

wherein:

L* is a neutral Lewis base;

(L*-H)$^+$ is a conjugate Bronsted acid of L*;

A$^{g-}$ is a noncoordinating, compatible anion having a charge of g–, and g is an integer from 1 to 3.

More preferably A$^{g-}$ corresponds to the formula: [M'Q$_4$]$^-$;

wherein:

M' is boron or aluminum in the +3 formal oxidation state; and

Q independently each occurrence is selected from hydride, dialkylamido, halide, hydrocarbyl, hydrocarbyloxide, halosubstituted-hydrocarbyl, halosubstituted hydrocarbyloxy, and halo-substituted silylhydrocarbyl radicals (including perhalogenated hydrocarbyl-perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433.

In a more preferred embodiment, d is one, that is, the counter ion has a single negative charge and is K. Activating cocatalysts comprising boron which are particularly useful in the preparation of catalysts of this invention may be represented by the following general formula:

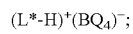

wherein:
L* is as previously defined;
B is boron in a formal oxidation state of 3; and
Q is a hydrocarbyl-, hydrocarbyloxy-, fluorinated hydrocarbyl-, fluorinated hydrocarbyloxy-, or fluorinated silylhydrocarbyl-group of up to 20 nonhydrogen atoms, with the proviso that in not more than one occasion is Q hydrocarbyl.

Preferred Lewis base salts are ammonium salts, more preferably trialkylammonium salts containing one or more $C_{12-40}$ alkyl groups. Most preferably, Q is each occurrence a fluorinated aryl group, especially, a pentafluorophenyl group.

Illustrative, but not limiting, examples of boron compounds which may be used as an activating cocatalyst in the preparation of the improved catalysts of this invention are tri-substituted ammonium salts such as:
trimethylammonium tetrakis(pentafluorophenyl) borate,
triethylammonium tetrakis(pentafluorophenyl) borate,
tripropylammonium tetrakis(pentafluorophenyl) borate,
tri(n-butyl)ammonium tetrakis(pentafluorophenyl) borate,
tri(sec-butyl)ammonium tetrakis(pentafluorophenyl) borate,
N,N-dimethylanilinium tetrakis(pentafluorophenyl) borate,
N,N-dimethylanilinium n-butyltris(pentafluorophenyl) borate,
N,N-dimethylanilinium benzyltris(pentafluorophenyl) borate,
N,N-dimethylanilinium tetrakis(4-(t-butyldimethylsilyl)-2,3,5,6-tetrafluorophenyl) borate,
N,N-dimethylanilinium tetrakis(4-(triisopropylsilyl)-2,3,5,6-tetrafluorophenyl) borate,
N,N-dimethylanilinium pentafluorophenoxytris(pentafluorophenyl) borate,
N,N-diethylanilinium tetrakis(pentafluorophenyl) borate,
N,N-dimethyl-2,4,6-trimethylanilinium tetrakis(pentafluorophenyl) borate,
dimethyloctadecylammonium tetrakis(pentafluorophenyl) borate,
methyldioctadecylammonium tetrakis(pentafluorophenyl) borate,
dialkyl ammonium salts such as:
di-(i-propyl)ammonium tetrakis(pentafluorophenyl) borate,
methyloctadecylammonium tetrakis(pentafluorophenyl) borate,
methyloctadodecylammonium tetrakis(pentafluorophenyl) borate, and
dioctadecylammonium tetrakis(pentafluorophenyl) borate;
tri-substituted phosphonium salts such as:
triphenylphosphonium tetrakis(pentafluorophenyl) borate,
methyldioctadecylphosphonium tetrakis(pentafluorophenyl) borate, and
tri(2,6-dimethylphenyl)phosphonium tetrakis(pentafluorophenyl) borate;
di-substituted oxonium salts such as:
diphenyloxonium tetrakis(pentafluorophenyl) borate,
di(o-tolyl)oxonium tetrakis(pentafluorophenyl) borate, and
di(octadecyl)oxonium tetrakis(pentafluorophenyl) borate;
di-substituted sulfonium salts such as:
di(o-tolyl)sulfonium tetrakis(pentafluorophenyl) borate, and
methylcotadecylsulfonium tetrakis(pentafluorophenyl) borate.

Preferred (L*-H)+ cations are methyldioctadecylammonium cations, dimethyloctadecylammonium cations, and ammonium cations derived from mixtures of trialkyl amines containing one or 2 $C_{14-18}$ alkyl groups.

Another suitable ion forming, activating cocatalyst comprises a salt of a cationic oxidizing agent and a noncoordinating, compatible anion represented by the formula:

$$(Ox^{h+})_g(A^{g-})_h,$$

wherein:
$Ox^{h+}$ is a cationic oxidizing agent having a charge of h+;
h is an integer from 1 to 3; and
$A^{g-}$ and g are as previously defined.

Examples of cationic oxidizing agents include: ferrocenium, hydrocarbyl-substituted ferrocenium, $Ag^+$, or $Pb^{+2}$. Preferred embodiments of $A^{g-}$ are those anions previously defined with respect to the Bronsted acid containing activating cocatalysts, especially tetrakis(pentafluorophenyl)borate.

Another suitable ion forming, activating cocatalyst comprises a compound which is a salt of a carbenium ion and a noncoordinating, compatible anion represented by the formula:

$$[C]^+A^-$$

wherein:
$[C]^+$ is a $C_{1-20}$ carbenium ion; and
$A^-$ is a noncoordinating, compatible anion having a charge of −1. A preferred carbenium ion is the trityl cation, that is triphenylmethylium.

A further suitable ion forming, activating cocatalyst comprises a compound which is a salt of a silylium ion and a noncoordinating, compatible anion represented by the formula:

$$(Q^1_3Si)^+A^-$$

wherein:
$Q^1$ is $C_{1-10}$ hydrocarbyl, and $A^-$ is as previously defined.
Preferred silylium salt activating cocatalysts are trimethylsilylium tetrakispentafluorophenylborate, triethylsilylium tetrakispentafluorophenylborate and ether substituted adducts thereof. Silylium salts have been previously generically disclosed in *J. Chem. Soc. Chem. Comm.*, 1993, 383-384, as well as Lambert, J. B., et al., *Organometallics*, 1994, 13, 2430-2443. The use of the above silylium salts as activating cocatalysts for addition polymerization catalysts is disclosed in U.S. Pat. No. 5,625,087.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433.

Suitable activating cocatalysts for use herein also include polymeric or oligomeric alumoxanes, especially methylalumoxane (MAO), triisobutyl aluminum modified methylalumoxane (MMAO), or isobutylalumoxane; Lewis acid modified alumoxanes, especially perhalogenated tri(hydrocarbyl)aluminum- or perhalogenated tri(hydrocarbyl)boron modified alumoxanes, having from 1 to 10 carbons in each hydrocarbyl or halogenated hydrocarbyl group, and most especially tris(pentafluorophenyl)borane modified alumoxanes. Such cocatalysts are previously disclosed in U.S. Pat. Nos. 6,214,760, 6,160,146, 6,140,521, and 6,696,379.

A class of cocatalysts comprising non-coordinating anions generically referred to as expanded anions, further disclosed in U.S. Pat. No. 6,395,671, may be suitably employed to activate the metal complexes of the present invention for olefin polymerization. Generally, these cocatalysts (illustrated by those having imidazolide, substituted imidazolide, imidazolinide, substituted imidazolinide, benzimidazolide, or substituted benzimidazolide anions) may be depicted as follows:

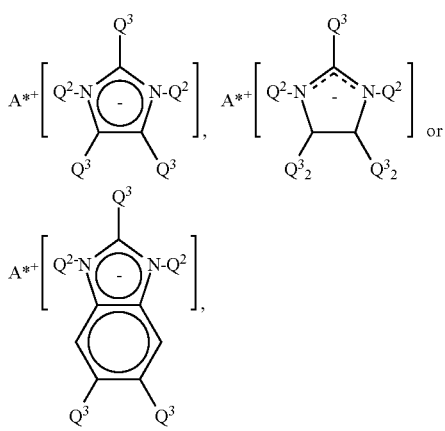

wherein:
A*+ is a cation, especially a proton containing cation, and preferably is a trihydrocarbyl ammonium cation containing one or two $C_{10-40}$ alkyl groups, especially a methyldi($C_{14-20}$ alkyl)ammonium cation, $Q^3$, independently each occurrence, is hydrogen or a halo, hydrocarbyl, halocarbyl, halohydrocarbyl, silylhydrocarbyl, or silyl, (including mono-, di- and tri(hydrocarbyl)silyl) group of up to 30 atoms not counting hydrogen, preferably $C_{1-20}$ alkyl, and $Q^2$ is tris(pentafluorophenyl)borane or tris(pentafluorophenyl)alumane).

Examples of these catalyst activators include trihydrocarbylammonium-salts, especially, methyldi($C_{14-20}$alkyl)ammonium-salts of:
bis(tris(pentafluorophenyl)borane)imidazolide,
bis(tris(pentafluorophenyl)borane)-2-undecylimidazolide,
bis(tris(pentafluorophenyl)borane)-2-heptadecylimidazolide,
bis(tris(pentafluorophenyl)borane)-4,5-bis(undecyl)imidazolide,
bis(tris(pentafluorophenyl)borane)-4,5-bis(heptadecyl)imidazolide,
bis(tris(pentafluorophenyl)borane)imidazolinide,
bis(tris(pentafluorophenyl)borane)-2-undecylimidazolinide,
bis(tris(pentafluorophenyl)borane)-2-heptadecylimidazolinide,
bis(tris(pentafluorophenyl)borane)-4,5-bis(undecyl)imidazolinide,
bis(tris(pentafluorophenyl)borane)-4,5-bis(heptadecyl)imidazolinide,
bis(tris(pentafluorophenyl)borane)-5,6-dimethylbenzimidazolide,
bis(tris(pentafluorophenyl)borane)-5,6-bis(undecyl)benzimidazolide,
bis(tris(pentafluorophenyl)alumane)imidazolide,
bis(tris(pentafluorophenyl)alumane)-2-undecylimidazolide,
bis(tris(pentafluorophenyl)alumane)-2-heptadecylimidazolide,
bis(tris(pentafluorophenyl)alumane)-4,5-bis(undecyl)imidazolide,
bis(tris(pentafluorophenyl)alumane)-4,5-bis(heptadecyl) imidazolide,
bis(tris(pentafluorophenyl)alumane)imidazolinide,
bis(tris(pentafluorophenyl)alumane)-2-undecylimidazolinide,
bis(tris(pentafluorophenyl)alumane)-2-heptadecylimidazolinide,
bis(tris(pentafluorophenyl)alumane)-4,5-bis(undecyl)imidazolinide,
bis(tris(pentafluorophenyl)alumane)-4,5-bis(heptadecyl) imidazolinide,
bis(tris(pentafluorophenyl)alumane)-5,6-dimethylbenzimidazolide, and
bis(tris(pentafluorophenyl)alumane)-5,6-bis(undecyl)benzimidazolide.

Other activators include those described in PCT publication WO 98/07515 such as tris(2,2',2"-nonafluorobiphenyl)fluoroaluminate. Combinations of activators are also contemplated by the invention, for example, alumoxanes and ionizing activators in combinations, see for example, EP-A-0 573120, PCT publications WO 94/07928 and WO 95/14044 and U.S. Pat. Nos. 5,153,157 and 5,453,410. WO 98/09996 describes activating catalyst compounds with perchlorates, periodates and iodates, including their hydrates. WO 99/18135 describes the use of organoboroaluminum activators. WO 03/10171 discloses catalyst activators that are adducts of Bronsted acids with Lewis acids. Other activators or methods for activating a catalyst compound are described in for example, U.S. Pat. Nos. 5,849,852, 5,859,653, 5,869,723, EP-A-615981, and PCT publication WO 98/32775. All of the foregoing catalyst activators as well as any other known activator for transition metal complex catalysts may be employed alone or in combination according to the present invention.

The molar ratio of catalyst/cocatalyst employed preferably ranges from 1:10,000 to 100:1, more preferably from 1:5000 to 10:1, most preferably from 1:1000 to 1:1. Alumoxane, when used by itself as an activating cocatalyst, is employed in large quantity, generally at least 100 times the quantity of metal complex on a molar basis. Tris(pentafluorophenyl)borane, where used as an activating cocatalyst is employed in a molar ratio to the metal complex of from 0.5:1 to 10:1, more preferably from 1:1 to 6:1 most preferably from 1:1 to 5:1. The remaining activating cocatalysts are generally employed in approximately equimolar quantity with the metal complex.

In some embodiments, wherein the group E contains oxygen, the invention also comprises a method of making a catalyst comprising brominating a substituted benzene to obtain a substituted dibromo benzene; oxidizing the substituted dibromo benzene to a substituted bromophenol via organometallic and organoboron intermediates; alkylating the substituted bromophenol to form a bromo aryl ether which contains a pendant olefin; reacting the bromo aryl ether with alkyl lithium and an alkyl borate to obtain an aryl boronic acid or ester which contains a pendant olefin; reacting the aryl boronic acid or ester with a bromo pyridine-imine under Suzuki coupling conditions to obtain an arylpyridine imine which contains a pendant olefin; alkylation of the olefinic alkoxy-substituted arylpyridine imine with a Grignard or other organometallic reagent to obtain an olefinic alkoxy-substituted arylpyridine amine; reacting the olefinic alkoxy-substituted arylpyridine amine with an alkyl lithium, metal halide and a Grignard reagent to obtain a snap-shut catalyst. Each step may be accomplished by methods known to one skilled in the art for generally carrying out each particular type of reaction. It is envisioned that the exact sequence of these reactions may be performed in different orders as is apparent to one skilled in the art.

In some embodiments, the invention also comprises a method of making a catalyst wherein the group E contains an atom other than oxygen. In these cases, the method comprises tethering an olefin to the substituted bromobenzene ring through an appropriate linking group E. Preferably, when the heteroatom of Group E is nitrogen, the olefin is tethered by alkylation of nitrogen with an olefinically substituted alkylating agent. Pendant olefins connected by carbon linkers may be introduced by alkylation using methods which are known to those skilled in the art. The method further comprises metalating the resulting bromobenzenes which contain a pendent olefin with alkyl lithium to produce an aryllithium intermediate; reacting the aryllithium intermediate with an alkyl borate to obtain an aryl boronic acid or ester which contains a pendant olefin; reacting the aryl boronic acid or ester with a bromo pyridine-imine under Suzuki coupling conditions to obtain an arylpyridine imine which contains a pendant olefin; alkylating the olefinic-substituted arylpyridine imine with a Grignard or other organometallic reagent to obtain an olefinic-substituted arylpyridine amine; reacting the olefinic-substituted arylpyridine amine with an alkyl lithium, metal halide and a Grignard reagent to obtain a snap shut catalyst. Each step may be accomplished by methods known to one skilled in the art for generally carrying out each particular type of reaction. It is envisioned that the exact sequence of these reactions may be performed in different orders as is apparent to one skilled in the art.

In some embodiments, the invention also comprises a method of making a catalyst wherein a different unsaturated group is inserted instead of a pendant olefin. Examples of other pendant moieties which can function similarly to a pendant olefin in the synthesis as described in the previous paragraph include imines, carbonitriles, ketones, aldehydes, isonitriles, esters, amides, cyanates, isocyanates, thiocyanates, and isothiocyanates.

In some embodiments, the catalyst of the invention further comprises, or is further prepared from, an inorganic or organic particulated solid support, wherein the catalyst is in supporting operative contact with the particulated solid support to give a supported catalyst. In these embodiments, the supported catalyst comprises a heterogeneous catalyst.

The solid support is any material that supports the invention catalyst and allows the resulting supported catalyst to catalyze polymerization of a polymerizable olefin. Examples of particulated solids are silica, silica gel, alumina, clays, expanded clays (aerogels), aluminosilicates, trialkylaluminum compounds, and organic or inorganic polymeric materials, especially polyolefins such as, for example, a poly(tetrafluoroethylene). More preferably, the inventive catalyst and solid support are employed in the supported catalyst in amounts that provide a ratio of (weight of the catalyst of the second embodiment (based on metal M)):weight of the solid support) of from 1:106 to 1:103, more preferably from 1:106 to 1:104.

The present invention also comprises a process comprising contacting the invention catalysts with polymerizable olefins under olefin-polymerizing conditions to produce polyolefins and the polyolefins resulting therefrom.

The term "olefin-polymerizing conditions" means reaction parameters such as, for example, temperature, pressure, concentration of olefin monomer(s), solvent(s), if any, reaction time, and reaction atmosphere sufficient to produce at least 5 mole percent yield of a polyolefin therefrom. In some embodiments, polymerization of olefins are accomplished using known conditions for Ziegler-Natta or Kaminsky-Sinn type olefin polymerization reactions. Preferably the conditions are at a temperature of from about −100° C. to about 300° C., more preferably at least about 0° C., still more preferably at least about 20° C., even more preferably at least about 50° C.; and more preferably about 250° C. or less, still more preferably about 200° C. or less, still more preferably about 150° C. or less; and under a pressure from about 0.5 atmosphere (50 kilopascals (kPa) to 10,000 atmospheres (1,010,000 kPa), more preferably at least about 1 atmosphere (101 kPa), still more preferably at least about 10 atmospheres (1010 kPa); and more preferably 1000 atmospheres (101,000 kPa) or less, still more preferably 500 atmospheres (50,500 kPa) or less; preferably under a dry inert atmosphere (e.g., dry nitrogen, argon, or helium); with mixing (e.g., agitating, stiffing, or shaking) for a time sufficient to produce the polyolefin (e.g., as determined by assaying an aliquot of a reaction mixture).

In some embodiments, the metal complexes of this invention are supported on a solid support as described herein and used in olefin polymerization processes in a slurry or a gas phase polymerization. As a practical limitation, slurry polymerization preferably takes place in liquid diluents in which the polymer product is substantially insoluble (e.g., less than 50 milligrams of polymer product dissolves in 1.0 milliliter of liquid diluent at 25° C.). Preferably, the diluent for slurry polymerization is one or more hydrocarbons with less than 5 carbon atoms. In some embodiments, one or more saturated hydrocarbons such as ethane, propane or butane are used in whole or part as the diluent. In other embodiments, an alpha-olefin monomer or a mixture of different alpha-olefin monomers are used in whole or part as the diluent. Most preferably, at least a major part of the diluent comprises the alpha-olefin monomer or monomers to be polymerized. In some embodiments, a dispersant, particularly an elastomer, is dissolved in the diluent, preferably utilizing techniques known in the art.

In some embodiments, suspension, solution, slurry, gas phase, solid state powder polymerization or other process condition are employed. In other embodiments, a solid support is employed in the form of a supported catalyst, as described above, preferably when the supported catalysts are used in a gas phase polymerization process. In most polymerization reactions, the ratio of (moles of invention catalyst): (total moles of polymerizable compounds employed) is from 10-12:1 to 10-1:1, more preferably from 10-9:1 to 10-5:1.

The present invention catalysts, whether or not supported in any suitable manner, preferably are used to polymerize a polymerizable olefin, or co-polymerize two or more polymerizable olefins, to prepare a polyolefin. The term "polymerizable olefin" means an ethylenically unsaturated monomer or ethylenically unsaturated polyolefin prepared therefrom, wherein each monomer or ethylenically unsaturated polyolefin comprises at least one carbon-carbon double bond and independently has from 2 to 100,000 carbon atoms, preferably 50,000 carbon atoms or less, more preferably 10,000 carbon atoms or less. Thus, polymerizable olefins include long chain macromolecular alpha-olefin units that are vinyl terminated polymeric remnants formed in situ during continuous solution polymerization reactions. In some aspects of the embodiment, such long chain macromolecular alpha-olefin units are readily polymerized along with ethylene and other short chain olefin monomers to give a polyolefin having long chain branching.

In some embodiments, a polymerization process of the invention employs one or more of the invention catalysts and at least one additional homogeneous or heterogeneous polymerization catalyst, either in the same reactor or in separate reactors, preferably connected in series or in parallel, to prepare polymer blends having desirable properties. A general description of such a process is disclosed in PCT International Patent Application Publication Number WO 94/00500.

In some embodiments, the polymerization is carried out as a batchwise or a continuous polymerization process. A continuous process is preferred, in which process, for example, invention catalyst, ethylene, a co-monomer olefin other than ethylene, and optionally a solvent, diluent, dispersant, or combination thereof are essentially continuously supplied to the reaction zone, and resulting polyolefin product is essentially continuously removed therefrom.

Without limiting in any way the scope of the invention, an illustrative means for carrying out such an essentially continuous polymerization process is as follows. In a stirred-tank reactor, the monomer olefins to be polymerized are introduced continuously, together with solvent and an optional chain transfer agent such as, for example, a stream of hydrogen introduced to the reactor. The reactor contains a liquid phase composed substantially of monomers, together with any solvent or additional diluent and dissolved polymer. In other embodiments, a small amount of a "H"-branch-inducing diene such as norbornadiene, 1,7-octadiene, or 1,9-decadiene is also added. Invention catalyst and activating cocatalyst are continuously introduced in the reactor liquid phase. In some embodiments, reactor temperature and pressure are controlled by, for example, adjusting solvent/monomer ratio, adjusting invention catalyst addition rate, cooling or heating the reactor liquid phase (e.g., using coils, jackets or both), or a combination thereof. In some embodiments, rate of polymerization is controlled by adjusting rate of invention catalyst addition. In some embodiments, ethylene content of a polymer product thereof is varied by adjusting the ratio of ethylene to comonomer olefin in the reactor, which ratio preferably is controlled by manipulating the respective feed rates of the monomers to the reactor. In some embodiments, molecular weight of polymer product is controlled by adjusting temperature, adjusting monomer concentration, or with the previously mention chain transfer agent. In some embodiments, reactor effluent is contacted with a catalyst kill agent such as water. A resulting polyolefin product solution is optionally heated, and the polyolefin is recovered by devolatilizing, e.g., flashing off volatiles such as gaseous monomers, residual solvent, and diluents at reduced pressure. In some embodiments, further devolatilization is conducted in equipment such as a devolatilizing extruder. In a continuous process, mean residence time of the invention catalyst and polyolefin product in the reactor preferably is from about 5 minutes to about 8 hours, and more preferably from about 10 minutes to about 6 hours.

In some embodiments, the catalysts of the present invention are employed in the production of ethylene homopolymers and ethylene/alpha-olefin copolymers having high levels of long chain branching. The use of the catalysts of the present invention in continuous polymerization processes, especially continuous, solution polymerization processes, allows for elevated reactor temperatures, which favor the formation of vinyl terminated polymer chains. In some embodiments, vinyl terminated polymer chains are incorporated into a growing polymer, thereby giving a polymer comprising a long chain branch. The use of the present catalysts advantageously allows for the production of ethylene/alpha-olefin copolymers having processability similar to high pressure, free radical produced low density polyethylene.

In some embodiments, the process is particularly suited for preparing ethylene homopolymers and ethylene/alpha-olefin copolymers. Generally such polymers have densities from 0.85 grams per milliliter (g/mL) to 0.96 g/mL. In some embodiments, a comonomer-to-monomer ratio of moles of alpha-olefin comonomer to moles of ethylene used in the polymerization is varied in order to adjust the density of the resulting polymer. When producing polyolefins with a density range of from 0.91 g/mL to 0.93 g/mL, preferably the comonomer-to-monomer ratio is less than 0.2, more preferably less than 0.05, still more preferably less than 0.02, and even more preferably less than 0.01. In some embodiments, hydrogen has been found to effectively control the molecular weight of the resulting polymer. In some embodiments, the ratio of moles of hydrogen to moles of monomer is less than about 0.5, preferably less than 0.2, more preferably less than 0.05, still more preferably less than 0.02 and even more preferably less than 0.01.

Preferably, each polymerizable olefin independently is ethylene; a linear or branched alpha-olefin of from about 3 to about 20 carbon atoms such as, for example, propylene, isobutylene, 1-butene, 1-pentene, 1-hexene, 3-methyl-1-pentene, 4-methyl-1-pentene, 1-octene, 1-decene, long chain macromolecular α-olefins, and mixtures thereof; an acyclic diene such as, for example, 1,4-butadiene, 1,4-hexadiene, and 1,7-octadiene; a cyclic olefin such as, for example, cyclobutene, cyclopentene, norbornene, and norbornene derivatives that are substituted in the 5- and 6-positions with ($C_1$-$C_{20}$)hydrocarbyl groups; a cyclic diene hydrocarbon of from about 4 to about 40 carbon atoms such as, for example, a cyclohexadiene, ethylidene-norbornene, and norbornadiene; an aromatic ring-substituted olefin of from 8 to 20 carbon atoms (e.g., styrene, ($C_1$-$C_4$)alkyl-substituted styrenes, and 4-phenylbutene); a vinyl monomer that is, for example, 4-vinylcyclohexene, divinylbenzene, and mixtures thereof with ethylene, an acrylonitrile, maleic acid ester, vinyl acetate, acrylate ester, methacrylate ester, or vinyl trialkyl silane; and mixtures thereof such as mixtures of ethylene and styrene, mixtures of ethylene, propylene, and styrene; mixtures of ethylene, styrene or propylene, and 1,4-hexadiene or a non-conjugated diene, especially ethylidene-norbornene.

Other novel compositions of the present invention include the catalyst which may be synthesized as described above optionally mixed with ethylene, an α-olefin, a reaction product or a mixture thereof.

The catalyst described above may also be used to produce an ethylene/α-olefin multi-block interpolymer such as those describe in, for example, U.S. application Ser. No. 11/376,835 filed on Mar. 15, 2006 and PCT Publication No. WO 2005/090427, filed on Mar. 17, 2005, which in turn claims priority to U.S. Provisional Application No. 60/553,906, filed Mar. 17, 2004. For purposes of United States patent practice, the contents of the aforementioned applications are herein incorporated by reference in their entirety. A shuttling agent such as diethyl zinc or others described in PCT Publication No. WO 2005/090427 will usually be employed. Such processes will typically then result in a polymer wherein the polymer has one or more of the following characteristics:

(1) an average block index greater than zero and up to about 1.0 and a molecular weight distribution, Mw/Mn, greater than about 1.3; or (2) at least one molecular fraction which elutes between 40° C. and 130° C. when fractionated using TREF, characterized in that the fraction has a block index of at least 0.5 and up to about 1; or (3) an Mw/Mn from about 1.7 to about 3.5, at least one melting point, Tm, in degrees Celsius, and a density, d, in grams/cubic centimeter, wherein the numerical values of Tm and d correspond to the relationship:

$$T_m > -2002.9 + 4538.5(d) - 2422.2(d)^2, \text{preferably}$$
$$T_m \geq 858.91 - 1825.3(d) + 1112.8(d)^2; \text{ or}$$

(4) an Mw/Mn from about 1.7 to about 3.5, and is characterized by a heat of fusion, ΔH in J/g, and a delta quantity, ΔT, in degrees Celsius defined as the temperature difference between the tallest DSC peak and the tallest CRYSTAF peak, wherein the numerical values of ΔT and ΔH have the following relationships:

$$\Delta T > -0.1299(\Delta H) + 62.81 \text{ for } \Delta H \text{ greater than zero and up to } 130 \text{ J/g,}$$

$$\Delta T \geq 48° \text{ C. for } \Delta H \text{ greater than } 130 \text{ J/g,}$$

wherein the CRYSTAF peak is determined using at least 5 percent of the cumulative polymer, and if less than 5 percent of the polymer has an identifiable CRYSTAF peak, then the CRYSTAF temperature is 30° C.; or (5) an elastic recovery, Re, in percent at 300 percent strain and 1 cycle measured with a compression-molded film of the ethylene/α-olefin interpolymer, and has a density, d, in grams/cubic centimeter, wherein the numerical values of Re and d satisfy the following relationship when ethylene/α-olefin interpolymer is substantially free of a cross-linked phase:

$$Re > 1481 - 1629(d); \text{ or}$$

(6) a molecular fraction which elutes between 40° C. and 130° C. when fractionated using TREF, characterized in that the fraction has a molar comonomer content of at least 5 percent higher than that of a comparable random ethylene interpolymer fraction eluting between the same temperatures, wherein said comparable random ethylene interpolymer has the same comonomer(s) and has a melt index, density, and molar comonomer content (based on the whole polymer) within 10 percent of that of the ethylene/α-olefin interpolymer; or (7) a storage modulus at 25° C., G'(25° C.), and a storage modulus at 100° C., G'(100° C.), wherein the ratio of G'(25° C.) to G'(100° C.) is in the range of about 1:1 to about 9:1.

Applications and End Uses

The polymers of the present invention can be used in a variety of conventional thermoplastic fabrication processes to produce useful articles. Such articles include objects comprising at least one film layer, such as a monolayer film, or at least one layer in a multilayer film prepared by cast, blown, calendered, or extrusion coating processes; molded articles, such as blow molded, injection molded, or rotomolded articles; extrusions; fibers; and woven or non-woven fabrics. The polymers described herein are also useful for wire and cable coating operations, as well as in sheet extrusion for vacuum forming operations, and forming molded articles, including the use of injection molding, blow molding process, or rotomolding processes. Compositions comprising the olefin polymers can also be formed into fabricated articles such as those previously mentioned using conventional polyolefin processing techniques which are well known to those skilled in the art of polyolefin processing. Dispersions, both aqueous and non-aqueous, can also be formed using the polymers or formulations comprising the same. Frothed foams comprising the invented polymers can also be formed, as disclosed in PCT application No. PCT/US2004/027593, filed Aug. 25, 2004, and published as WO2005/021622. The polymers may also be crosslinked by any known means, such as the use of peroxide, electron beam, silane, azide, or other cross-linking technique. The polymers can also be chemically modified, such as by grafting (for example by use of maleic anhydride (MAH), silanes, or other grafting agent), halogenation, amination, sulfonation, or other chemical modification.

Suitable end uses for the foregoing products include elastic films and fibers; soft touch goods, such as tooth brush handles and appliance handles; antiblocking compositions; cap liners, gaskets and profiles; adhesives (including hot melt adhesives and pressure sensitive adhesives); footwear (including shoe soles and shoe liners); auto interior parts and profiles; foam goods (both open and closed cell); impact modifiers for other thermoplastic polymers; coated fabrics; hoses; tubing; weather stripping; cap liners; flooring; and viscosity index modifiers, also known as pour point modifiers, for lubricants.

EXAMPLES

General Experimental Considerations

The term "overnight", if used, refers to a time of approximately 16-18 hours, the term "room temperature", refers to a temperature of 20-25° C., and the term "mixed alkanes" refers to a commercially obtained mixture of $C_{6-9}$ aliphatic hydrocarbons available under the trade designation Isopar E®, from ExxonMobil Chemical Company. In the event the name of a compound herein does not conform to the structural representation thereof, the structural representation shall control. The synthesis of all metal complexes and the preparation of all screening experiments are carried out in a dry nitrogen atmosphere using dry box techniques. All solvents used are HPLC grade and are dried before their use.

Unless specified otherwise, all reagents are handled under anaerobic conditions using standard procedures for the handling of extremely air- and water-sensitive materials. Solvents are used without further purification. All other chemicals are commercial materials and are used as received.

Testing Methods

In the examples that follow, the following analytical techniques are employed:

GPC Method (Excluding Samples 1-4 and A-C)

The gel permeation chromatographic system consists of either a Polymer Laboratories Model PL-210 or a Polymer Laboratories Model PL-220 instrument. The column and carousel compartments are operated at 140° C. Three Polymer Laboratories 10-micron Mixed-B columns are used. The solvent is 1,2,4 trichlorobenzene. The samples are prepared at a concentration of 0.1 grams of polymer in 50 milliliters of solvent containing 200 ppm of butylated hydroxytoluene (BHT). Samples are prepared by agitating lightly for 2 hours at 160° C. The injection volume used is 100 microliters and the flow rate is 1.0 ml/minute.

Calibration of the GPC column set is performed with 21 narrow molecular weight distribution polystyrene standards with molecular weights ranging from 580 to 8,400,000, arranged in 6 "cocktail" mixtures with at least a decade of separation between individual molecular weights. The standards are purchased from Polymer Laboratories (Shropshire, UK). The polystyrene standards are prepared at 0.025 grams in 50 milliliters of solvent for molecular weights equal to or greater than 1,000,000, and 0.05 grams in 50 milliliters of solvent for molecular weights less than 1,000,000. The polystyrene standards are dissolved at 80° C. with gentle agitation for 30 minutes. The narrow standards mixtures are run first and in order of decreasing highest molecular weight component to minimize degradation. The polystyrene standard peak molecular weights are converted to polyethylene molecular weights using the following equation (as described in Williams and Ward, J. Polym. Sci., Polym. Let., 6, 621 (1968)): $M_{polyethylene} = 0.431(M_{polystyrene})$.

Polyethylene equivalent molecular weight calculations are performed using Viscotek TriSEC software Version 3.0.

DSC Standard Method

Differential Scanning Calorimetry results are determined using a TAI model Q1000 DSC equipped with an RCS cooling accessory and an autosampler. A nitrogen purge gas flow of 50 ml/min is used. The sample is pressed into a thin film and melted in the press at about 175° C. and then air-cooled to room temperature (25° C.). 3-10 mg of material is then cut into a 6 mm diameter disk, accurately weighed, placed in a light aluminum pan (ca 50 mg), and then crimped shut. The thermal behavior of the sample is investigated with the following temperature profile. The sample is rapidly heated to 180° C. and held isothermal for 3 minutes in order to remove any previous thermal history. The sample is then cooled to −40° C. at 10° C./min cooling rate and held at −40° C. for 3 minutes. The sample is then heated to 150° C. at 10° C./min. heating rate. The cooling and second heating curves are recorded.

The DSC melting peak is measured as the maximum in heat flow rate (W/g) with respect to the linear baseline drawn between −30° C. and end of melting. The heat of fusion is measured as the area under the melting curve between −30° C. and the end of melting using a linear baseline.

Calibration of the DSC is done as follows. First, a baseline is obtained by running a DSC from −90° C. without any sample in the aluminum DSC pan. Then 7 milligrams of a fresh indium sample is analyzed by heating the sample to 180° C., cooling the sample to 140° C. at a cooling rate of 10° C./min followed by keeping the sample isothermally at 140° C. for 1 minute, followed by heating the sample from 140° C. to 180° C. at a heating rate of 10° C. per minute. The heat of fusion and the onset of melting of the indium sample are determined and checked to be within 0.5° C. from 156.6° C. for the onset of melting and within 0.5 J/g from 28.71 J/g for the of fusion. Then deionized water is analyzed by cooling a small drop of fresh sample in the DSC pan from 25° C. to −30° C. at a cooling rate of 10° C. per minute. The sample is kept isothermally at −30° C. for 2 minutes and heat to 30° C. at a heating rate of 10° C. per minute. The onset of melting is determined and checked to be within 0.5° C. from 0° C.

NMR Analysis.

NMR spectra ($^1$H, $^{13}$C, COSY, HSQC) were recorded on a Bruker Avance Spectrometer Operating at 400 MHz (for $^1$H) Using Standard Pulse Sequences.

Catalyst Example A is (1-(6-((2,6-Diisopropylphenylamido)(2-isopropylphenyl)-methyl)pyridin-2-yl)naphthalen-2-yl)hafnium(IV) dimethyl.

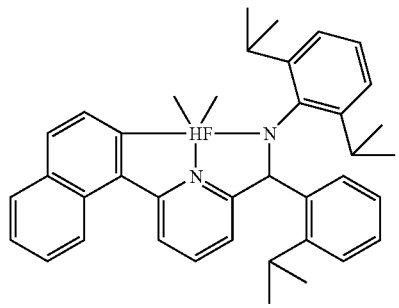

Synthesis of Catalyst Example 1-((5-(6-((2,6-diisopropylphenylamido)(phenyl)-methyl)pyridin-2-yl)-6,8-dimethylchroman-4-yl)methyl)hafnium(IV) dimethyl

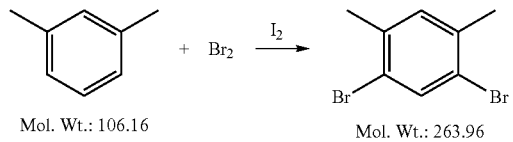

1,5-Dibromo-2,4-dimethylbenzene

A 100-mL round bottomed flask wrapped in aluminum foil is charged with m-xylene (40.0 mL, 328 mmol) and iodine (0.48 g, 1.90 mmol). The mixture is stirred for about an hour while cooling in an ice bath. Bromine (34 mL, 656 mmol) is added via dropping funnel over a period of one hour. After overnight reaction, potassium hydroxide (KOH) (20% aq, 150 mL) is added and the resulting mixture is heated gently using a heating mantle. The solid is melted and the biphasic mixture is stirred for about one hour as the yellow color slowly fades. After cooling, the liquid is decanted and the white solid is collected by filtration and washed with additional water (3×100 mL), then recrystallized from ethanol (250 mL). Yield=42.0 g (48.6%)

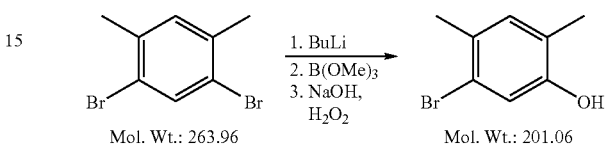

5-Bromo-2,4-dimethylphenol

In a glovebox, 1,5-dibromo-2,4-dimethylbenzene (10.000 g, 37.9 mmol) is dissolved in dry THF (140 mL) in a one-neck round bottomed flask with a thermometer well. The flask is capped with a septum, and removed from the glovebox. Nitrogen purge is provided via a needle through the septum, and the solution is cooled to −70° C. using a dry ice/acetone bath. Butyllithium (BuLi) (1.6M in hexanes, 26 mL, 42 mmol) is added slowly, maintaining the temperature below −65° C. After stirring for 80 minutes at −70° C., trimethylborate (B(OMe)$_3$) (4.2 mL, 37.9 mmol) is added slowly, maintaining the temperature below −62° C., and then the reaction is allowed to slowly warm to room temperature overnight. Solvents are removed on a rotovap, leaving a very pale yellow oily solid, which is dissolved in tetrahydrofuran (THF) (100 mL) and treated with hydrogen peroxide (H$_2$O$_2$) (30% aq, 13 mL) and sodium hydroxide (NaOH) (1M, 25 mL) for two hours. The reaction is then quenched with ammonium chloride (NH$_4$Cl) (aq) and extracted into ether (2×100 mL). The organic fractions are combined, dried over sodium sulfate, filtered and dried in vacuo. Yield=6.60 g (86.7%) of pale yellow waxy solid.

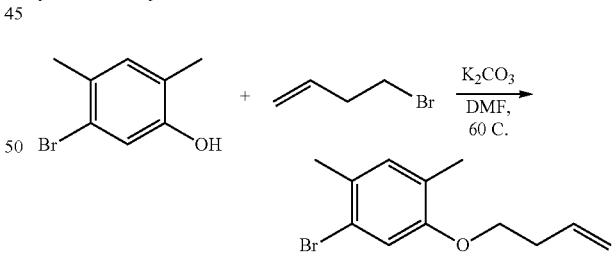

1-Bromo-5-(but-3-enyloxy)-2,4-dimethylbenzene

A 250-mL round bottomed flask is charged with 5-bromo-2,4-dimethylphenol (3.135 g, 15.6 mmol) and dimethylformamide (DMF) (50 mL). Potassium carbonate (23.7 g, 172 mmol) and bromobutene (15.8 mL, 156 mmol) are added and the reaction mixture is heated to 95° C. for 2 hr. After cooling to room temp, water (200 mL) is added. The product is extracted into ether (2×100 mL), and the combined organic fractions are washed with brine, dried over sodium sulfate and dried in vacuo. Yield=3.63 g (91.3%) of light yellow liquid.

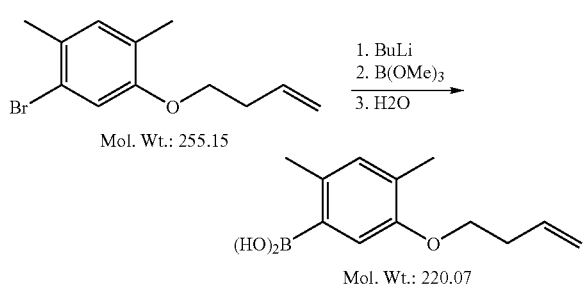

5-(But-3-enyloxy)-2,4-dimethylphenylboronic acid

In the glovebox, a 100-mL round bottomed flask is charged with 1-bromo-5-(but-3-enyloxy)-2,4-dimethylbenzene (3.142 g, 13.6 mmol) and THF (100 mL). The flask is sealed with a septum and removed from the glovebox. The flask is cooled to −70° C. under nitrogen purge. BuLi (1.6M in hexanes, 8.2 mL, 13 mmol) is added slowly, keeping the temperature below −68° C., and the reaction mixture is stirred for one hr at −70° C. Trimethylborate (1.3 mL, 12 mmol) is added, and the mixture is stirred as it slowly warms to room temperature. Solvents are removed on a rotovap, and ice (60 g) containing hydrochloric acid (HCl) (conc, 5 mL) is added, and then ether (60 mL). A white precipitate forms, and this is collected on a fine frit. Yield=1.283 g of a white solid. $^1$H NMR is taken by suspending the solid in $d_6$-dimethylsulfoxide ($d_6$-DMSO) and adding a trace of HCl.

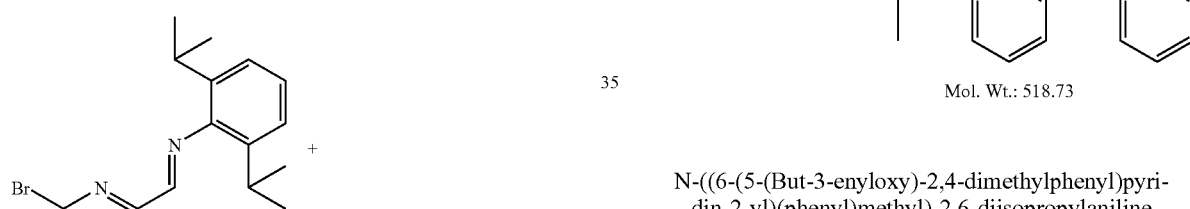

N-((6-(5-(But-3-enyloxy)-2,4-dimethylphenyl)pyridin-2-yl)methylene)-2,6-diisopropylaniline In the glovebox, N-((6-bromopyridin-2-yl)methylene)-2,6-diisopropylaniline (1.392 g, 4.03 mmol) is combined with 5-(but-3-enyloxy)-2,4-dimethylphenylboronic acid (1.000 g, 4.03 mmol) and KOH (0.678 g, 12.1 mmol) and dry THF (40 mL) is added. Palladium(I) tri-tert-butylphosphine bromide, dimer [P$^t$Bu$_3$)PdBr]$_2$ (0.062 g, 0.040 mmol) is added and the reaction mixture is stirred for five hours, removed from the glovebox, and ether (100 mL) is added. The solution is washed with water (50 mL) and then brine (50 mL), dried over magnesium sulfate, filtered, and solvents removed by evaporation. Yield=1.86 g of orange sticky oil. The product is used without further purification.

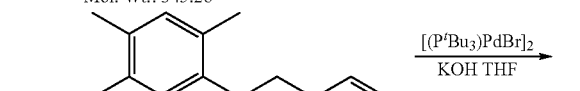

N-((6-(5-(But-3-enyloxy)-2,4-dimethylphenyl)pyridin-2-yl)(phenyl)methyl)-2,6-diisopropylaniline In the glovebox, N-((6-(5-(but-3-enyloxy)-2,4-dimethylphenyl)pyridin-2-yl)methylene)-2,6-diisopropylaniline (1.527 g, 3.40 mmol) is dissolved in toluene (40 mL). Phenylmagnesiumbromide (3.0M in ether, 1.36 mL, 4.09 mmol) is added, and the reaction mixture stirred at room temperature for one hour, removed from the glovebox, and quenched by addition of water (60 mL), and ether (80 mL). The aqueous layer is washed with additional ether (40 mL), and the combined organic fractions are washed with brine, dried over magnesium sulfate and filtered. Solvents are removed in vacuo, and the crude product is purified by column chromatography using 10:1 hexanes:ethylacetate ($R_f$=0.39) to yield 1.27 g (72.0%) of a very pale yellow solid. The structure is assigned by $^1$H NMR as shown in FIG. 1.

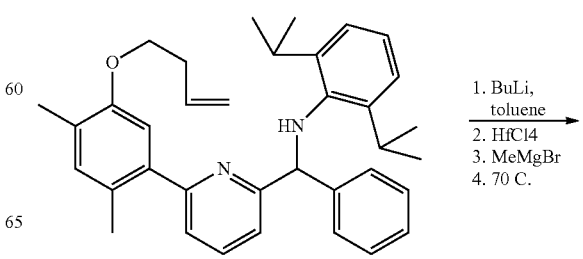

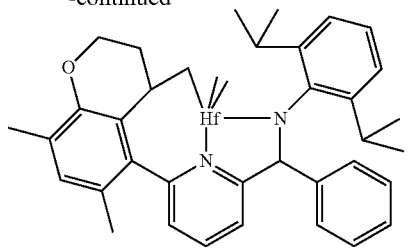

((5-(6-((2,6-Diisopropylphenylamido)(phenyl)methyl)pyridin-2-yl)-6,8-dimethylchroman-4-yl)methyl)hafnium (IV) dimethyl complex N-((6-(5-(But-3-enyloxy)-2,4-dimethylphenyl)pyridin-2-yl)(phenyl)methyl)-2,6-diisopropylaniline (0.500 g, 0.964 mmol) is dissolved in toluene (50 mL) and BuLi (1.6M in hexanes, 0.66 mL, 1.06 mmol) is added. After stirring for one hour, hafnium chloride (HfCl$_4$) (0.309 g, 0.964 mmol) is added. The reaction mixture is stirred overnight, and then methylmagnesium bromide (MeMgBr) (3.0M in ether, 0.19 mL, 0.58 mmol) is added. After two hours, solvents are removed in vacuo, toluene (20 mL) is added, and the mixture is filtered and washed with additional toluene (5 mL). The light orange filtrate solution is heated to 70-75° C. for 25 minutes, and then volatiles are removed in vacuo to yield 0.61 g (87%) of sticky red-orange solid. The initial reaction mixture shows multiple products, see NMR in FIG. 2, however, the olefinic resonances disappear as the ligand snaps shut (tethered monomer inserts into the Hf-aryl), as shown in FIG. 3. The structure is assigned by $^1$H, $^{13}$C, COSY and HSQC NMR (FIGS. 3-7).

General Reactor Polymerization Procedure

A 1 ga. (3.8 L) AE autoclave is purged at high temperature with N$_2$. Isopar®E is added, and the reactor is heated to 120° C. 1-Octene and hydrogen are added batchwise to the reactor and are not regulated during the run. The reactor is pressurized with ethylene (3.10 MPa). Solutions of the pre-catalyst, cocatalyst (1.2 equivalents to pre-catalyst), and a scavenger (5 equivalents to pre-catalyst) are mixed and then added to the reactor using a flush of high pressure Isopar® E. Polymer yield is kept low to minimize monomer composition drift during the experiment. After the prescribed reaction time, reactor contents are dumped into a resin kettle and mixed with Irganox®1010/Irgafos®168 stabilizer mixture (1 g). The polymer is recovered by evaporating the majority of the solvent at room temperature and then dried further in a vacuum oven overnight at 90° C. Following the run, the reactor is hot-flushed with Isopar®E to prevent polymer contamination from run to run.

As may be seen by the data above, catalyst performance is decoupled from the monomer. In particular, in comparing Runs 1 and 2, performed with Catalyst A, it may be seen that when the octene load is decreased by a factor of about 4, the polymer yield goes down by a factor of about 1.4. In comparing Runs 3 and 4, however, when the octene load is decreased, the polymer yield is only reduced by an insignificant amount.

It is also instructive to compare the kinetic profiles of the two catalysts in a polymerization reaction, as illustrated in FIG. 8, which shows temperature profiles for adiabatic octene polymerizations. Catalyst A lights off very slowly due to requisite reaction steps required prior to initiation of polymerization. However, catalyst 1 shows an immediate exotherm because it does not require in situ reaction steps prior to polymerization.

What is claimed is:
1. A metal complex corresponding to Formula (II):

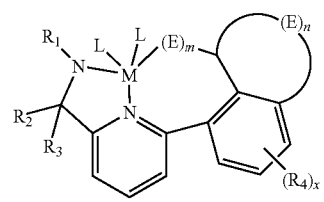

(II)

wherein L is a leaving group; M is a metal of any one of Groups 3 to 6 of the Periodic Table of the Elements being in a formal oxidation state of +2, +3, +4, +5, or +6; E is a linking group that is a divalent bridging group of from 1 to 41 atoms other than hydrogen; $R_1$, $R_2$, $R_3$ and $R_4$ are selected from alkyl, cycloalkyl, heteroalkyl, cycloheteroalkyl, aryl, heteroaryl or inertly substituted derivatives thereof; x is an integer from 1 to 4; and m and n are the integer 1.

2. The metal complex of claim 1 wherein the metal complex corresponds to any of the following formulas:

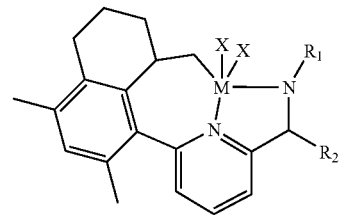

TABLE 1

Batch reactor ethylene/octene copolymerizations.

| Run # | Catalyst | Octene Load (g) | Polymer Yield (g) | g polymer/ g Hf | Tm (° C.) | Mn | Mw | Mw/Mn |
|---|---|---|---|---|---|---|---|---|
| 1 | A* | 250 | 60 | 96,000 | 69.3 | 200500 | 752700 | 3.75 |
| 2 | A* | 64 | 42 | 67,000 | 104.2 | 240100 | 787400 | 3.28 |
| 3 | 1 | 250 | 14 | 22,000 | 75.9 | 117700 | 463400 | 3.94 |
| 4 | 1 | 64 | 12 | 19,000 | 104.8 | 128400 | 444500 | 3.46 |

*comparative, not of the present invention

31
-continued
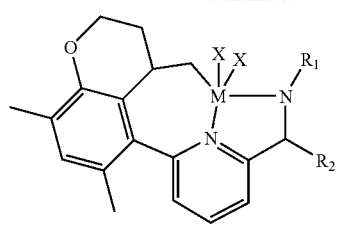
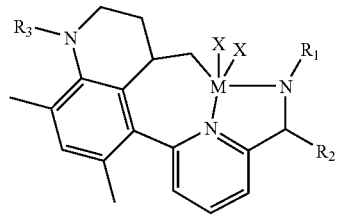
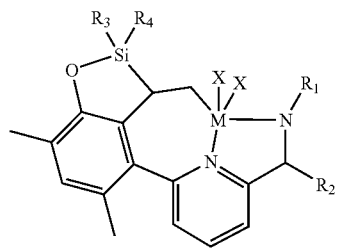
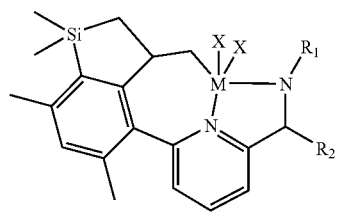
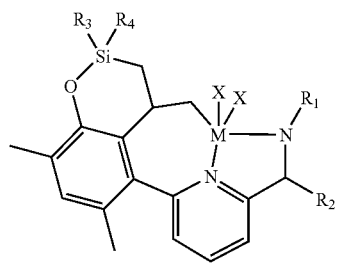
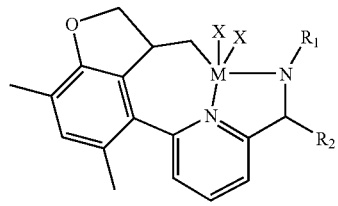
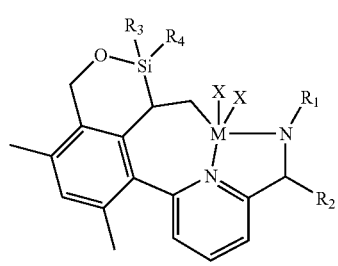
32
-continued
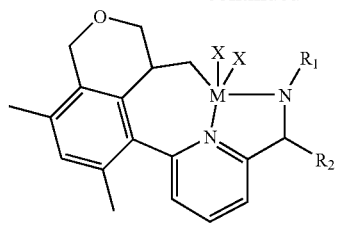
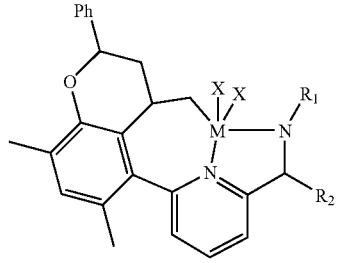
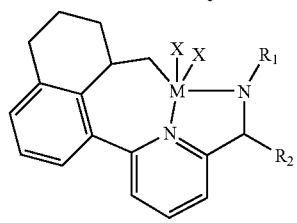
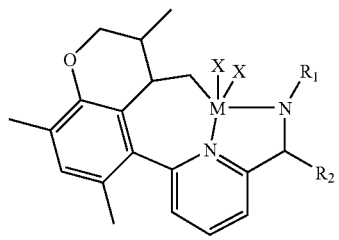
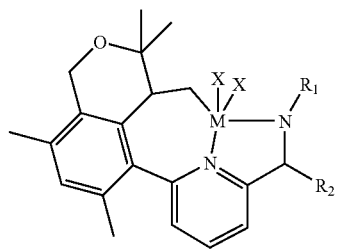
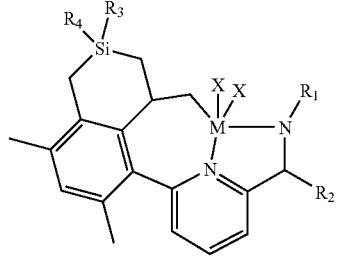
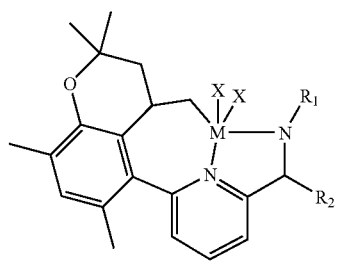

-continued

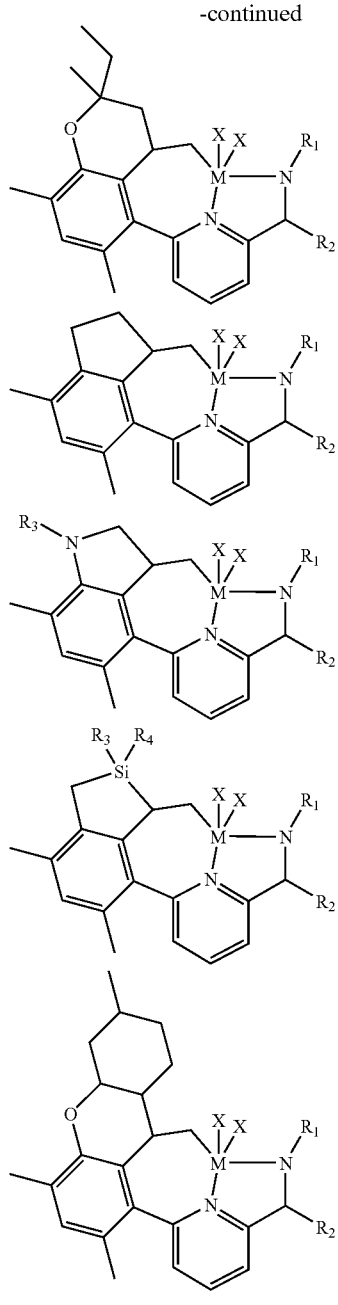

wherein M, $R_1$, $R_2$, $R_3$ and $R_4$ are as defined in claim 1; and, X is a leaving group.

3. The metal complex of claim 1 wherein the metal of Formula II is a Group 4 metal.

4. The metal complex of claim 1 wherein the metal of Formula II is hafnium.

5. The metal complex of claim 1 wherein E of Formula II is a mono- or di-$C_{1-20}$ hydrocarbyl substituted silane of methylene group (—$CR_2$—)$_n$ wherein R is any alkyl, aryl, heteroalkyl or heteroarylalkyl.

6. The metal complex of claim 1 wherein E of Formula II is a divalent bridging group of from 10 to 30 atoms not counting hydrogen, selected from mono- or di-aryl-substituted methylene or silylene groups or mono- or di-heteroaryl-substituted methylene or silylene groups, wherein at least one such aryl- or heteroaryl-substituent is substituted in one or both ortho-positions with a secondary or tertiary alkyl-group, a secondary or tertiary heteroalkyl group, a cycloalkyl group, or a heterocycloalkyl group.

7. The metal complex of claim 1 wherein L of Formula II is a halide, N,N-di($C_{1-4}$-alkyl)amido, $C_{7-10}$ aralkyl, $C_{1-20}$ alkyl, $C_{5-20}$ cycloalkyl, or tri($C_{1-4}$)alkylsilyl; a tri($C_{1-4}$)alkylsilyl-substituted $C_{1-10}$ hydrocarbyl group; or two L groups together are a $C_{4-40}$ conjugated diene.

8. A metal complex corresponding to any of the following formulas:

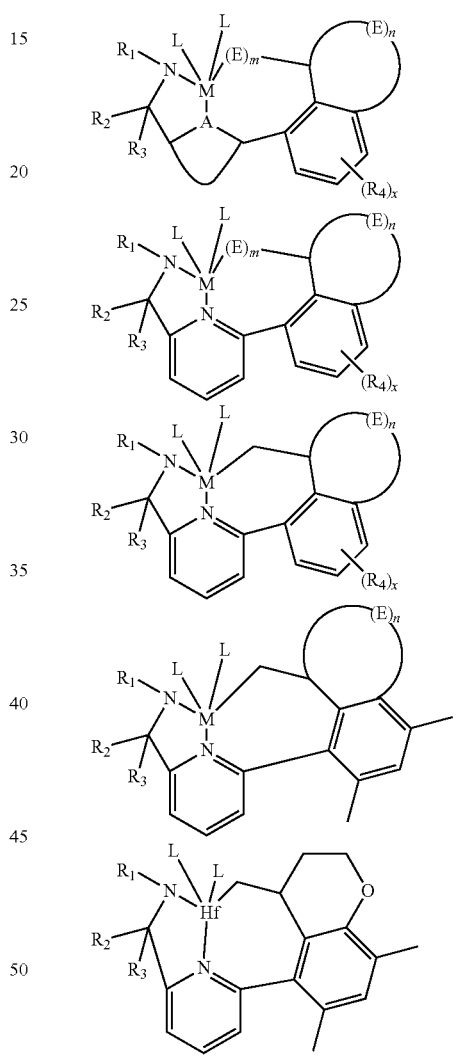

wherein M is a metal of any one of Groups 3 to 6 of the Periodic Table of the Elements being in a formal oxidation state of +2, +3, +4, +5, or +6; E is a linking group that is a divalent bridging group of from 1 to 41 atoms other than hydrogen; L is a leaving group, x is an integer of 1 to 4; m and n are the integer 1 and $R_1$, $R_2$, $R_3$ and $R_4$ are selected from alkyl, cycloalkyl, heteroalkyl, cycloheteroalkyl, aryl, heteroaryl or inertly substituted derivatives thereof.

* * * * *